US010393708B2

(12) United States Patent
Ovadia et al.

(10) Patent No.: US 10,393,708 B2
(45) Date of Patent: Aug. 27, 2019

(54) METHOD AND APPARATUS FOR INSPECTING A GAS SAMPLE

(71) Applicant: S.T.I. Security Technology Integration Ltd., Shefayim (IL)

(72) Inventors: Yuval Ovadia, Kibbutz Yagur (IL); Amos Linenberg, Sparta, NJ (US)

(73) Assignee: S.T.I. Security Technology Integration Ltd., Shefayim (IL)

( * ) Notice: Subject to any disclaimer, the term of this patent is extended or adjusted under 35 U.S.C. 154(b) by 517 days.

(21) Appl. No.: 15/006,156

(22) Filed: Jan. 26, 2016

(65) Prior Publication Data

US 2016/0139089 A1    May 19, 2016

Related U.S. Application Data

(63) Continuation of application No. 13/514,301, filed as application No. PCT/IL2010/001035 on Dec. 7, 2010, now Pat. No. 9,250,218.

(Continued)

(51) Int. Cl.
*G01N 30/30* (2006.01)
*G01N 30/08* (2006.01)
(Continued)

(52) U.S. Cl.
CPC .......... *G01N 30/30* (2013.01); *G01N 1/2214* (2013.01); *G01N 1/2273* (2013.01); *G01N 1/405* (2013.01);
(Continued)

(58) Field of Classification Search
CPC ..................................................... G01N 30/30
See application file for complete search history.

(56) References Cited

U.S. PATENT DOCUMENTS 3,585,860 A    6/1971  Alt
3,607,075 A    9/1971  Wolf
(Continued)

FOREIGN PATENT DOCUMENTS

EP         0511729         11/1992
WO    WO 2011/070574       6/2011

OTHER PUBLICATIONS

Office Action dated Dec. 15, 2016 From the Israel Patent Office Re. Application No. 220223 and Its Translation Into English. (4 Pages).
(Continued)

*Primary Examiner* — Son T Le
*Assistant Examiner* — Alex T Devito

(57) ABSTRACT

An apparatus for detecting a presence of at least one analyte in a gas sample. The apparatus comprises a pump for drawing a gas sample from an ambient air, a passage having first and second ends, a chamber connected to the first end and containing a concentrating element for collecting at least one analyte from the gas sample, a chromatographic separator connected to a second end of the passage, and a gas source for streaming a carrier gas via the chamber to transfer the at least one analyte toward at least one chemical detector, via the chromatographic separator, in a first direction. The pump draws the gas sample via the chamber in a second direction and the first and second directions are substantially opposing to one another.

17 Claims, 20 Drawing Sheets

Related U.S. Application Data

(60) Provisional application No. 61/267,138, filed on Dec. 7, 2009.

(51) Int. Cl.

| | | |
|---|---|---|
| *G01N 30/02* | (2006.01) | |
| *G01N 1/22* | (2006.01) | |
| *G01N 1/40* | (2006.01) | |
| *G01N 30/12* | (2006.01) | |
| *G01N 33/00* | (2006.01) | |
| *G01N 30/14* | (2006.01) | |
| *G01N 1/02* | (2006.01) | |

(52) U.S. Cl.
CPC ............. *G01N 30/02* (2013.01); *G01N 30/08* (2013.01); *G01N 30/12* (2013.01); *G01N 33/0057* (2013.01); *G01N 30/14* (2013.01); *G01N 2001/022* (2013.01); *G01N 2030/025* (2013.01); *G01N 2030/126* (2013.01)

(56) References Cited

U.S. PATENT DOCUMENTS

| | | | | |
|---|---|---|---|---|
| 3,992,271 | A | * 11/1976 | Danzig | ............ C25B 1/04 204/293 |
| 4,128,008 | A | 12/1978 | Linenberg | |
| 4,293,316 | A | * 10/1981 | Block | ............ G01N 1/34 73/31.07 |
| 4,600,581 | A | 7/1986 | Aldrich | |
| 4,711,957 | A | 12/1987 | Lai | |
| 5,027,643 | A | 7/1991 | Jenkins | |
| 5,098,451 | A | 3/1992 | Rounbehler et al. | |
| 5,141,534 | A | 8/1992 | Sacks et al. | |
| 5,289,715 | A | 3/1994 | Staples et al. | |
| 5,465,607 | A | 11/1995 | Corrigan et al. | |
| 5,469,369 | A | * 11/1995 | Rose-Pehrsson | .... G01N 29/022 340/632 |
| 5,739,422 | A | 4/1998 | Riviello et al. | |
| 5,827,945 | A | 10/1998 | Arnold | |
| 6,238,622 | B1 | 5/2001 | Salimian | |
| 6,319,723 | B1 | * 11/2001 | Jeffers | ............ G01N 1/40 422/82.02 |
| 7,282,676 | B1 | 10/2007 | Bouchier et al. | |
| 2005/0092109 | A1 | 5/2005 | Albro et al. | |
| 2008/0250877 | A1 | 10/2008 | Wu | |
| 2013/0125620 | A1 | 5/2013 | Ovadia et al. | |
| 2016/0139088 | A1 | 5/2016 | Ovadia et al. | |
| 2016/0146765 | A1 | 5/2016 | Ovadia et al. | |

OTHER PUBLICATIONS

Requisition by the Examiner dated Nov. 9, 2016 From the Canadian Intellectual Property Office Re. Application No. 2,819,395. (7 Pages).
Official Action dated Jul. 21, 2016 From the US Patent and Trademark Office Re. U.S. Appl. No. 15/005,032.
Office Action dated Jan. 19, 2016 From the Israel Patent Office Re. Application No. 220223 and Its Translation Into English.
Official Action dated May 30, 2017 From the US Patent and Trademark Office Re. U.S. Appl. No. 15/011,723. (19 pages).
Communication Pursuant to Rules 70(2) and 70a(2) EPC dated Apr. 24, 2014 From the European Patent Office Re. Application No. 10835607.2.
International Preliminary Report on Patentability dated Jun. 21, 2012 From the International Bureau of WIPO Re. Application No. PCT/IL2010/01035.
International Search Report and the Written Opinion dated Apr. 13, 2011 From the International Searching Authority Re. Application No. PCT/IL2010/01035.
Notice of Allowance dated Oct. 7, 2015 From the US Patent and Trademark Office Re. U.S. Appl. No. 13/514,301.
Official Action dated Apr. 16, 2015 From the US Patent and Trademark Office Re. U.S. Appl. No. 13/514,301.
Restriction Official Action dated Nov. 24, 2014 From the US Patent and Trademark Office Re. U.S. Appl. No. 13/514,301.
Supplementary European Search Report and the European Search Opinion dated Apr. 4, 2014 From the European Patent Office Re. Application No. 10835607.2.
Sanchez et al. "On-Line Multibed Sorption Trap and Injector for the GC Analysis of Organic Vapors in Large-Volume Air Samples", Analytical Chemistry, XP001171132, 75(4): 978-985, Feb. 15, 2003. Abstract, p. 979, col. 1, Line 20-p. 980, col. 2, Line 22, p. 981, col. 1, Lines 23-32, 51-54, p. 984, col. 2, Lines 7-14, 36-40, Figs. 1-2.
Examination Report Under Sections 12 & 13 of the Patents Act, 1970 and the Patents Rules, 2003 dated Apr. 18, 2018 From the Government of India, Intellectual Property India, Patents, Designs, Trade Marks, Geographical Indications Re. Application No. 1643/MUMNP/2012. (6 Pages).
Official Action dated Aug. 10, 2016 From the US Patent and Trademark Office Re. U.S. Appl. No. 15/011,723.
Communication Pursuant to Article 94(3) EPC Dated Apr. 8, 2019 From the European Patent Office Re. Application No. 10835607.2. (10 pages).

* cited by examiner

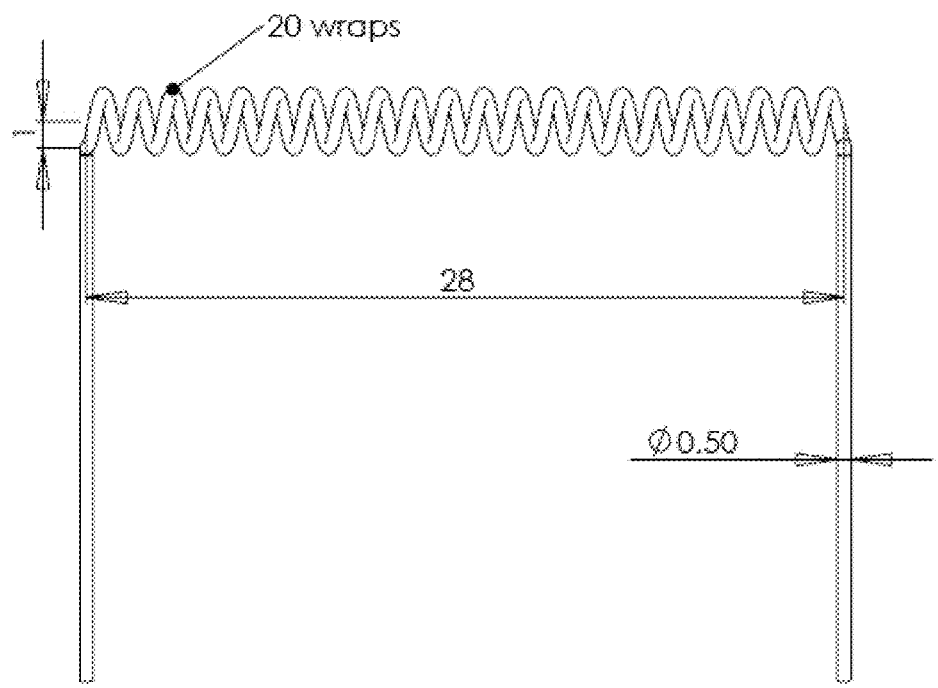
FIG. 6A
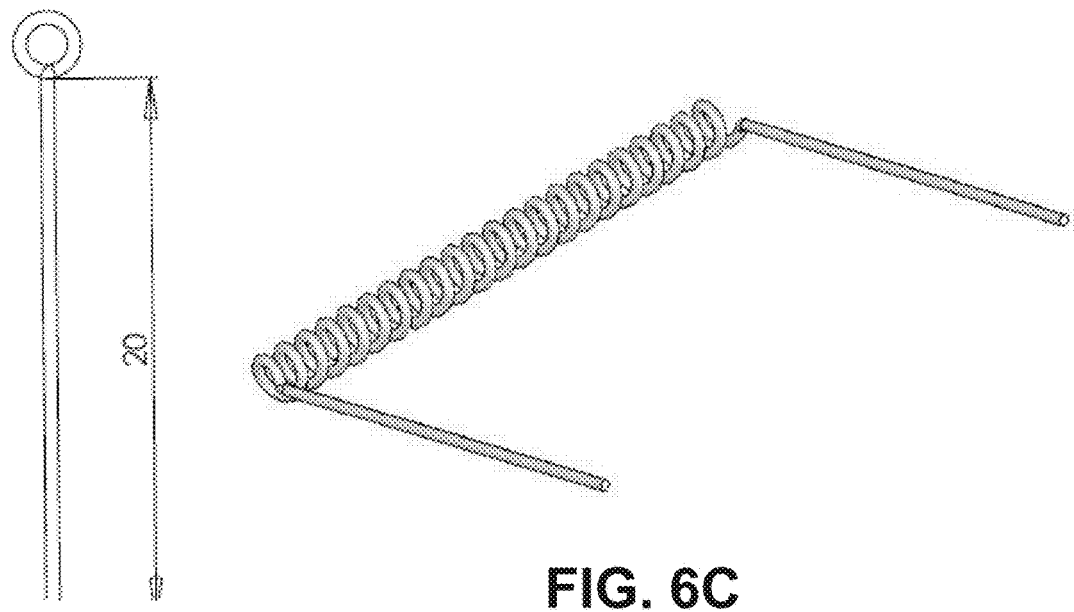
FIG. 6B
FIG. 6C

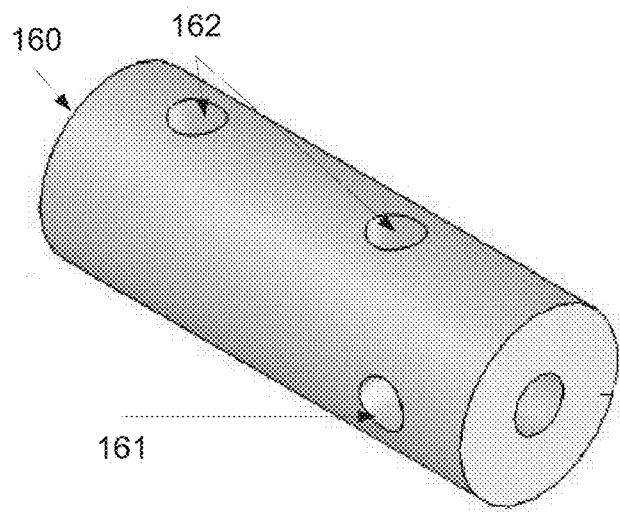
FIG. 7A
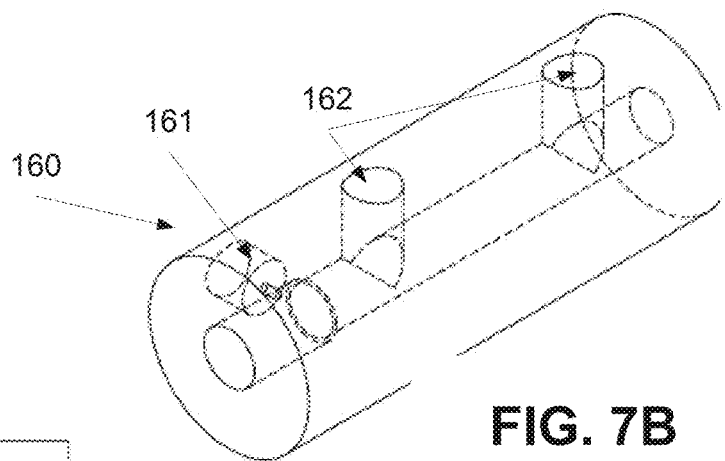
FIG. 7B
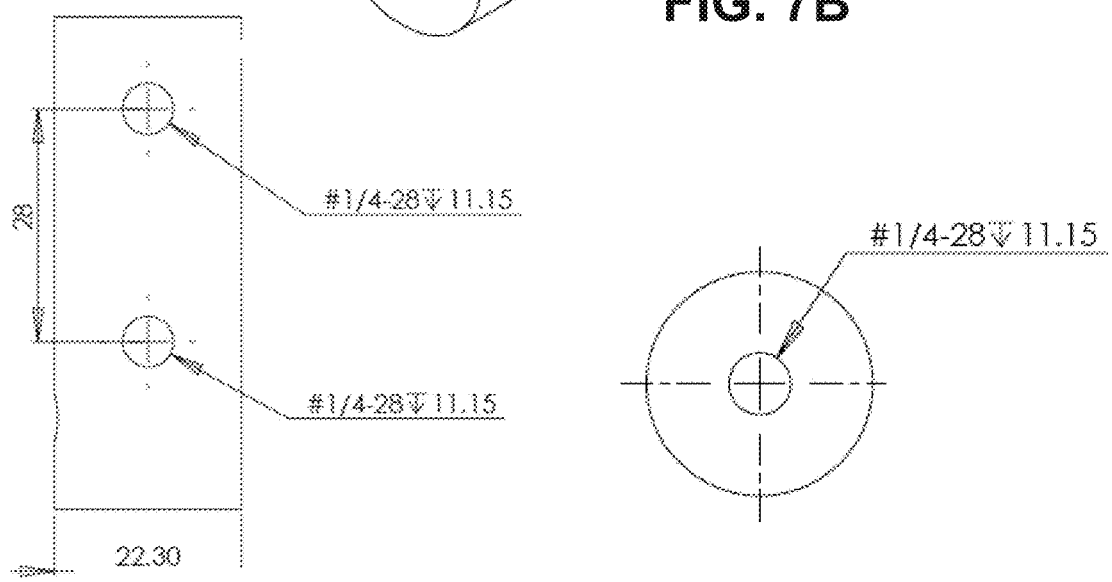
FIG. 7C  FIG. 7D

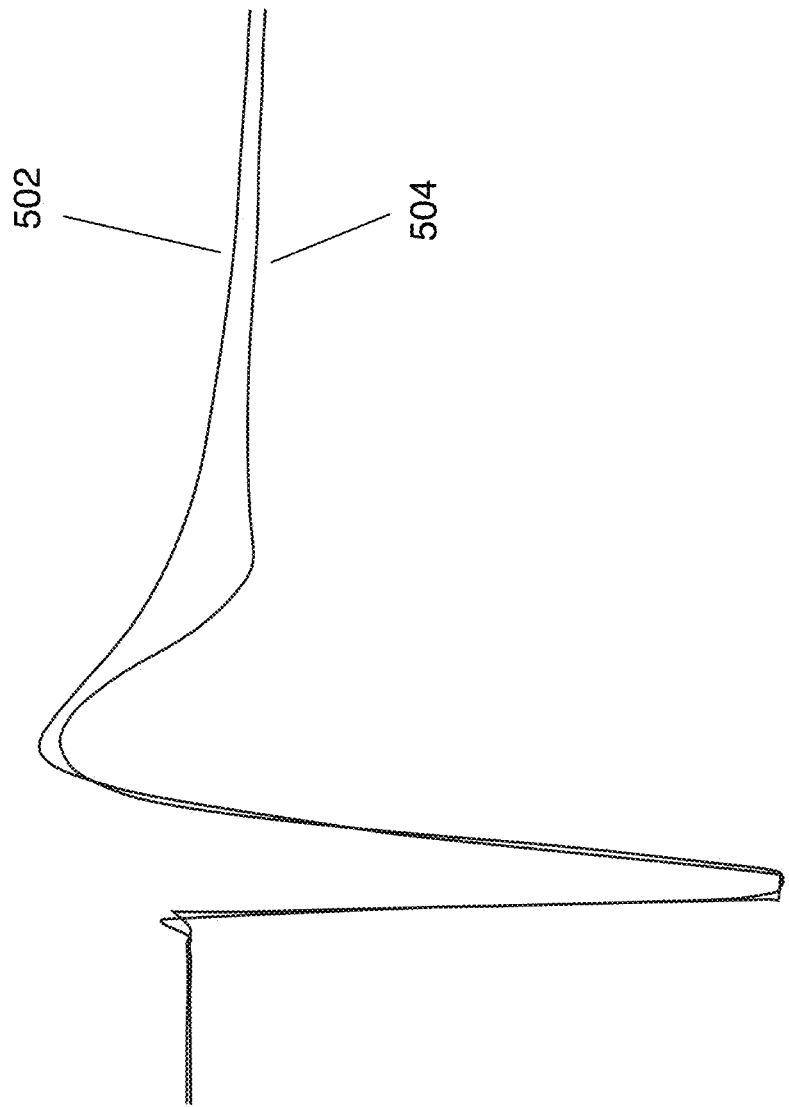

METHOD AND APPARATUS FOR INSPECTING A GAS SAMPLE

RELATED APPLICATIONS

This application is a continuation of U.S. patent application Ser. No. 13/514,301 filed on Nov. 13, 2012, which is a National Phase of PCT Patent Application No. PCT/IL2010/001035 having International filing date of Dec. 7, 2010, which claims the benefit of priority of U.S. Provisional Patent Application No. 61/267,138 filed on Dec. 7, 2009. The contents of the above applications are all incorporated herein by reference.

FIELD AND BACKGROUND OF THE INVENTION

The present invention, in some embodiments thereof, relates to system and method for detecting traces of chemical substances and, more particularly, but not exclusively, to system and method for detecting traces of chemical substances in a stream of gas.

Detection of molecules of organic and nonorganic chemical substances and/or compounds in gas samples is required for various applications, for example scientific applications, manufacturing process applications, and homeland security applications.

Several types of machines have been developed to detect trace signatures for chemical substances. A common technology for this application is ion mobility spectrometry (IMS). This method is similar to mass spectrometry (MS), where molecules are ionized and then moved in an electric field in a vacuum, except that IMS operates at atmospheric pressure. The time that it takes for an ion, in IMS, to move a specified distance in an electric field is indicative of that ion's size to charge ratio: ions with a larger cross section will collide with more gas at atmospheric pressure and will therefore be slower. Gas chromatography (GC) is often coupled to the detection methods in order to separate molecules before detection. This improves the performance of the chemical detecting unit and adds another dimension of data, as the time it takes for a molecule to pass through the GC may be used as an indicator of its identity. GC normally requires a bottled inert gas and GC columns.

During the last years, various systems and methods having high sensitivity for detecting traces of chemicals carried in the ambient air have been developed. Some of the systems and methods have an improved velocity since many of the applications prefer a complete analysis to be completed in less than a minute. These developments allow detecting the presence and/or the absence of one or more chemical substances by analyzing air samples and detecting trace concentrations in less than a minute. For example, U.S. Patent Application Number 2008/0250877, published on Oct. 16, 2008 describes a sample collection method that releases and collects residues of explosives and other chemicals from a surface. This method is implemented into a compact detection system that can be used as a "wand" for screening chemicals residues on a subject. The wand configuration includes multi-function for sampling and detecting multiple threads. The invention further describes a method of inspecting a subject using an interrogating apparatus in a sweeping motion; the near range closed loop particle sampling arrangement allows effective collection of particle and vapor residues from a targeted surface. The invention also describes a sampling and detecting apparatus for on-the-fly threat detection using compact ion mobility based detectors.

SUMMARY OF THE INVENTION

According to some embodiments of the present invention, there is provided a method for inspecting a gas sample. The method comprises a) drawing a gas sample through a chamber having a concentration element so as to allow at least one analyte from the gas sample to be bonded thereto, b) extracting impurities from the chamber by streaming a carrier gas toward a first outlet therethrough, c) heating the concentration element to release the at least one bonded analyte, d) streaming the carrier gas via the chamber so as to carry the at least one released analyte toward a second outlet, via a chromatographic separator and a detection unit, and e) reading an output of the detection unit for detecting at least one of the presence, the absence and the concentration of the at least one analyte.

Optionally, the streaming is performed during a period of less than 10 seconds.

Optionally, the b)-e) are performed in less than 20 seconds.

Optionally, the b)-e) are performed in less than 10 seconds.

Optionally, the method further comprises f) cooling the concentration element in less than 10 seconds.

More optionally, the a)-f) are iteratively performed in detection cycles of less than 1 minute.

Optionally, the heating comprises increasing the temperature of the concentration element to at least 200° C. in less than 2 seconds.

Optionally, the b) is performed in less than 1 second.

Optionally, the carrier gas and the gas sample are streamed in substantially opposing directions in the chamber.

According to some embodiments of the present invention, there is provided an apparatus for detecting a presence of at least one analyte in a gas sample. The apparatus comprises a pump for drawing a gas sample from an ambient air, a passage having first and second ends, a chamber connected to the first end and containing a concentrating element for collecting at least one analyte from the gas sample, a chromatographic separator connected to a second end of the passage, and a gas source for streaming a carrier gas via the chamber to transfer the at least one analyte toward at least one chemical detector, via the chromatographic separator, in a first direction. The pump draws the gas sample via the chamber in a second direction, the first and second directions being substantially opposing to one another.

Optionally, the diameter of the chromatographic separator having a diameter of less than 2 mm.

Optionally, the diameter of the passage is less than 1 mm.

Optionally, the passage is valveless.

Optionally, the chromatographic separator having a density selected for diverting the gas sampling and facilitating the passage of the carrier gas.

Optionally, the pump draws the gas sample via an inlet between the first and second ends on the passage.

Optionally, the chromatographic separator comprises a gas chromatograph (GC) column for separating at least one chemical substance from the streamed carrier gas; wherein the at least one analyte and the at least one chemical substance are different.

More optionally, the gas chromatograph element comprising Silicon OV 275.

More optionally, the Silicon OV 275 is in a 5% concentration.

More optionally, the gas chromatograph element is supported on Chromosorb® 80-100 mesh.

Optionally, the at least one chemical detector comprises an electron capturer.

Optionally, the concentrating element comprises a platinum coil for bonding the at least one analyte.

Optionally, the concentrating element is coated with a layer comprising OV-17 silicone.

Optionally, the at least one analyte consisting at least one of polynitro aromatics, nitrate esters, nitramines, nitrate salts, chlorates, peroxides, and energetic materials.

Optionally, the apparatus further comprises a handheld housing sized and shaped to contain the pump, the passage, the chamber, the chromatographic separator, and the gas source.

Optionally, the apparatus further comprises a heater for maintaining the at least one chemical detector and the chromatographic separator in a working temperature.

Optionally, the apparatus further comprises an additional gas source for drawing a gas via the at least one detector during the streaming.

Optionally, the having an aperture for facilitating the streaming.

According to some embodiments of the present invention, there is provided a gas concentration device. The gas concentration device comprises a chamber, an inlet for drawing a gas sample stream via the chamber, a metallic concentrator positioned in the chamber and substantially coated with a layer comprising methyl-phenylsilicones so as to append at least one analyte from the gas sample stream, and a heating element for heating the metallic concentrator so as to release the at least one analyte from the metallic concentrator.

Optionally, the methyl-phenylsilicones comprising OV-17 silicone.

Optionally, the OV-17 silicone is in a concentration of between 3% and 10%.

Optionally, the OV-17 silicone is in a concentration of 5%.

According to some embodiments of the present invention, there is provided a method for inspecting a gas sample stream. The method comprises a) streaming a gas sample in chamber containing a concentration element so that at least one analyte from the gas sample being bonded thereto, b) streaming a carrier gas in the chamber, toward at least one detector, to transfer the at least one analyte to the at least one detector, and c) analyzing the at least one analyte by using the detection element. The carrier gas and the gas sample are streamed in opposing directions in the chamber.

Optionally, the method further comprises d) streaming amount of the carrier gas in the chamber so that reminders of the at least one analyte being removed therefrom.

Optionally, the method further comprises heating the concentration element before the b) to catalyze a release of the at least one analyte from the concentration element.

Optionally, the method further comprises streaming an amount of the carrier gas via the at least one detector so that reminders of the at least one analyte being removed therefrom.

According to some embodiments of the present invention, there is provided a method for inspecting a gas sample stream. The method comprises a) heating a chemical detector to a standby temperature and maintaining the chemical detector in the standby temperature, b) collecting at least one analyte from a gas sample using a concentration element in a chamber while streaming a first amount of carrier gas into a target space of a chemical detector so as to maintain the standby temperature during the collecting, and c) streaming a second amount of carrier gas via the chamber so that the at least one analyte being transferred into the target space after the b).

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volitile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 6A-6C are schematic illustrations of an exemplary platinum coil, according to some embodiments of the present invention;

FIGS. 7A-7D are schematic illustrations of an exemplary chamber of a concentration unit, according to some embodiments of the present invention;

FIGS. 11A-11F are graphs of reference time-dependent curves and exemplary respective time-dependent curves of output signals received from a chemical detector in response to molecules of various explosives.

DESCRIPTION OF EMBODIMENTS OF THE INVENTION

Figure 1:
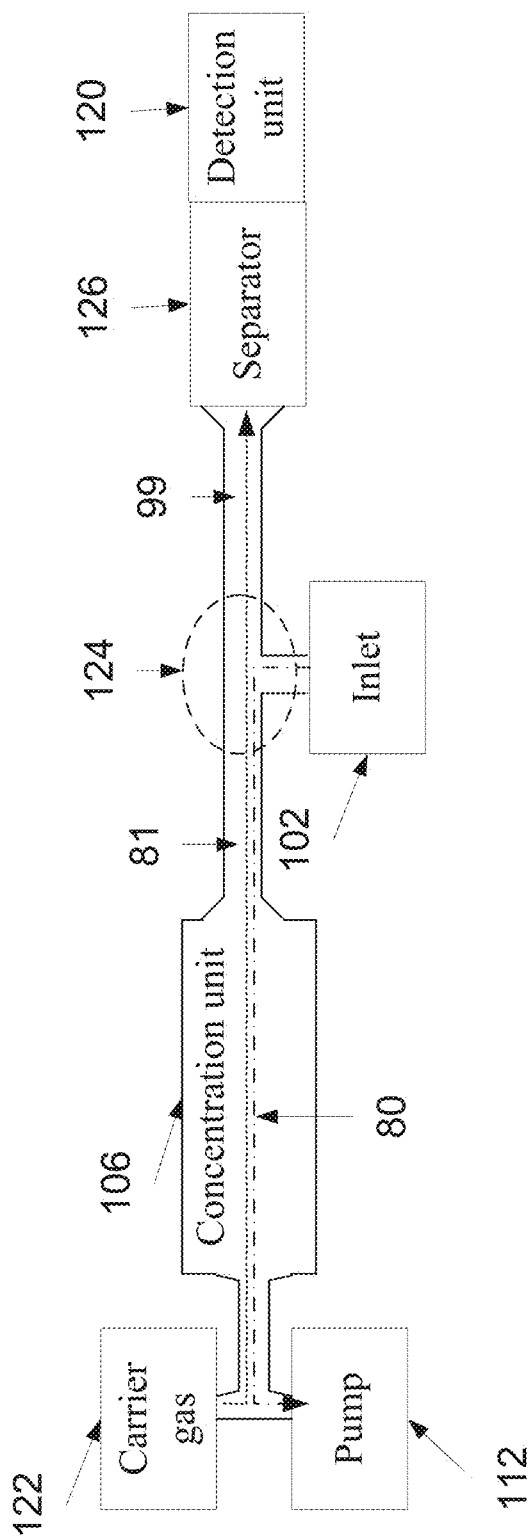
FIG. 1 is a schematic illustration of an apparatus for detecting a presence of a chemical substance, according to some embodiments of the present invention.

The present invention, in some embodiments thereof, relates to system and method for detecting traces of chemical substances and, more particularly, but not exclusively, to system and method for detecting traces of chemical substances in a stream of gas.

According to some embodiments of the present invention there is provided an apparatus for detecting a presence of one or more analytes in a gas sample. The method comprises a pump, or any other mechanical device that moves gas by pressure or suction, that streams a sample of gas, such as a sample of ambient air into the device, and a concentrating element for collecting, for example by bonding, analytes, such as chemical substances and compounds, from the gas sample. The concentrating element is connected, via a passage, optionally valveless, to a detection unit that includes one or more chemical detectors, optionally via a chromatographic separator, such CG column, optionally about 105 mm long, and/or a gas membrane. The concentrating element is further connected to a gas source that streams, therethrough, carrier gas toward the detection unit. The carrier gas collects the bonded analytes, which are optionally released by heating the concentrating element, and transfers them to the chemical detectors for the probing thereof. As the gas source and the chemical detectors are optionally located in different sizes of the concentration element, the carrier gas and the gas sample are streamed via the concentrating element, and optionally via at least a portion of the passage, in substantially opposite directions.

According to some embodiments of the present invention, there is provided a concentration element for gas inspection devices that comprises a metallic element coated with a layer of methyl-phenylsilicones, such as OV-17 silicone. Optionally, the layer includes the OV-17 silicone in a concentration of between 3% and 10%, for example 5%.

According to some embodiments of the present invention, an apparatus having one or more chemical detectors which are continuously heated is provided, for example nickel 63 electron capture detectors. The continuous heating of the detectors, and optionally the chromatographic separator that is used for increasing their efficiency, are maintained in a working temperature during a standby period, for example of more than 10 minutes. In such a manner, the device may switch from a standby mode to an operational mode during which a sample of gas is inspected, in less than 6 seconds, for example 2 seconds.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Reference is now made to FIG. 1, which is a schematic illustration of an analysis apparatus 100 for detecting a presence of one or more chemical substances, according to some embodiments of the present invention. As used herein a chemical substance or an analyte means one or more chemical substances, chemical compounds, and/or chemical elements. For example, the chemical substance may include polynitro aromatics, nitrate esters, nitramines, nitrate salts, chlorates, peroxides, and/or any other energetic materials, such as explosives, for example low vapor pressure explosives such as trinitrotoluene (TNT), Cyclotrimethylenetrinitramine (RDX), pentaerythritol tetranitrate (PETN), and cyclotetramethylene-tetranitramine (HMX).

The analysis apparatus 100 includes an aperture 102 for receiving a gas sample, for example from the ambient air, and a concentrating unit 106, such as a chamber or a lumen that includes a concentrating element of the concentrating unit 106, optionally metallic, such as a preconcentrator module, for example a coil or a porous element, such as a screen or a mesh, for collecting analytes from the gas sample, for example as described below. Optionally, the concentrating element is a heatable coil having a diameter and a length that is selected according to the analytes which are selected to be analyzed by the analysis apparatus 100.

The analysis apparatus 100 further includes a detector 120 that includes one or more chemical detectors. Optionally, the detector 120 includes a chemical detector such as an electron capture detector (ECD), such as nickel 63 electron capture detector. Optionally, the electron capture detector is used for detecting the analytes in the carrier gas stream. Optionally, the ECD uses a radioactive beta particle (electron) emitter, such as a metal foil holding 10-15 millicuries of the radionuclide nickel-63. Additionally or alternatively, other chemical detectors may be used for example an ion mobility spectrometer (IMS), a mass spectrometer (MS), a surface acoustic wave chemical detector (SAW), a differential mobility spectrometer (DMS), and chemiluminescence detector (CLD), gas chromatograph (GC), and thermo redox detectors.

Optionally, a chemical detector, such as an electron capture detector, is used for detecting the analytes which are passing through a chromatographic separator 126, such as a CG column and/or a gas membrane, for example as described below. Optionally, the CG column is relatively short, for example between 76 mm and 153 mm, for instance 105 mm. Optionally, the diameter of the CG column is about 3 mm and the diameter of the internal lumen thereof is about 1.5 mm. The chromatographic separator 126 selectively separates molecules from a gas that is streamed therethrough, for example compounds and substances which are different from the analytes inspected by the analysis apparatus 100. In such a manner, the relative proportion of the analytes among the molecules which are passing in front of the detector 120 increases.

Optionally, the chemical detectors of the detector 120 generate a signal that is read substantially continuously. In such a manner, the baseline of the chemical detectors may be reset according to changes in the atmosphere, the ambient temperature, the atmospheric pressure, and/or a wear and/or a deformation of the chemical detector. Such a resetting calibrates the reading of the chemical detectors and reduces the probability of false detection or false misdetection. It should be noted that the false detection rate using a device as outlined above and described in relation to FIGS. 2, 4, 5 and 8 has been estimated about 0.01%.

Figure 4:
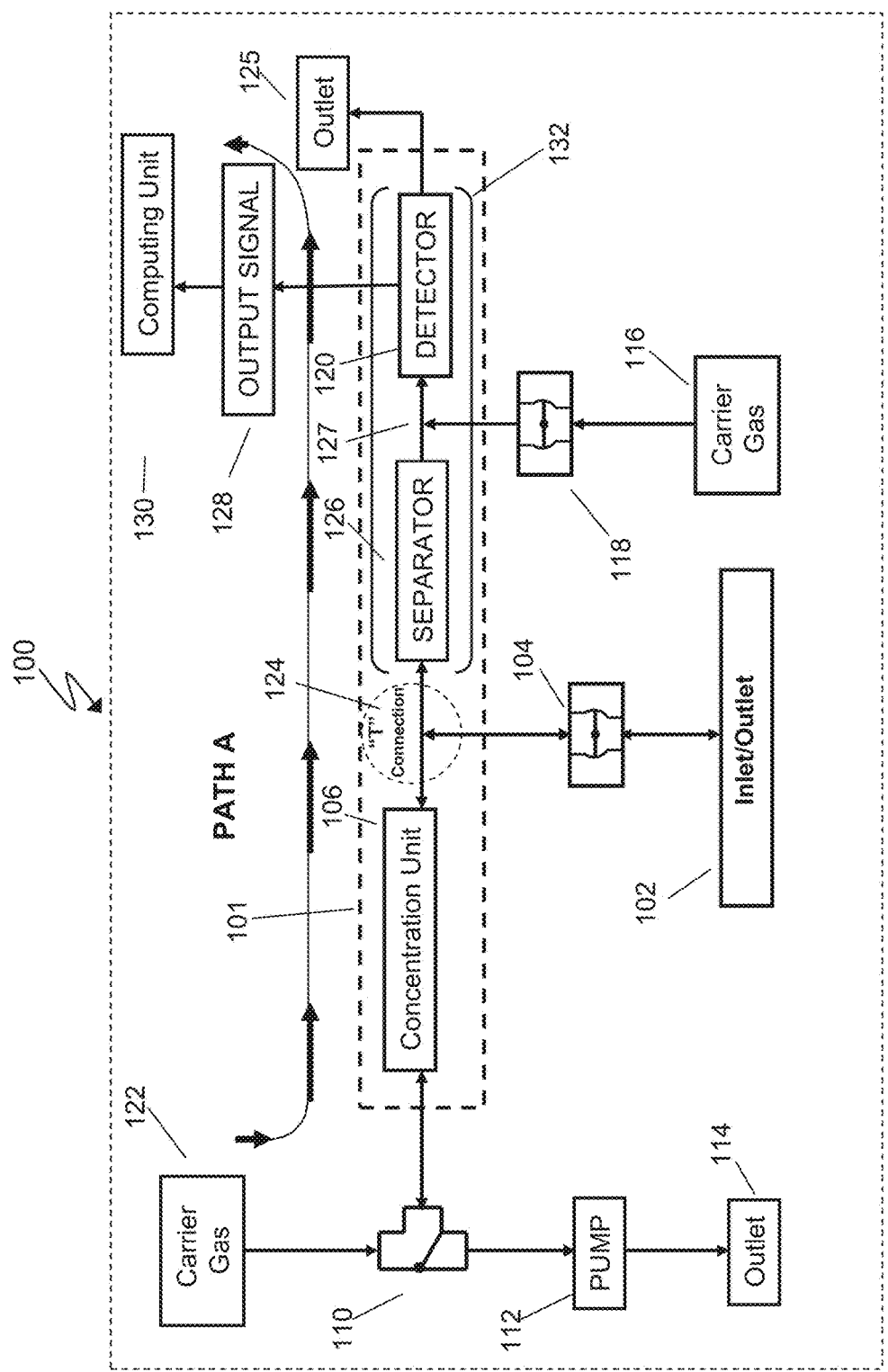
FIG. 4 is a schematic illustration of the apparatus of FIG. 2 wherein inert gas is streamed from a utility/carrier gas source, via a chromatographic separator and a detection unit, toward an outlet, according to some embodiments of the present invention.
Figure 5:
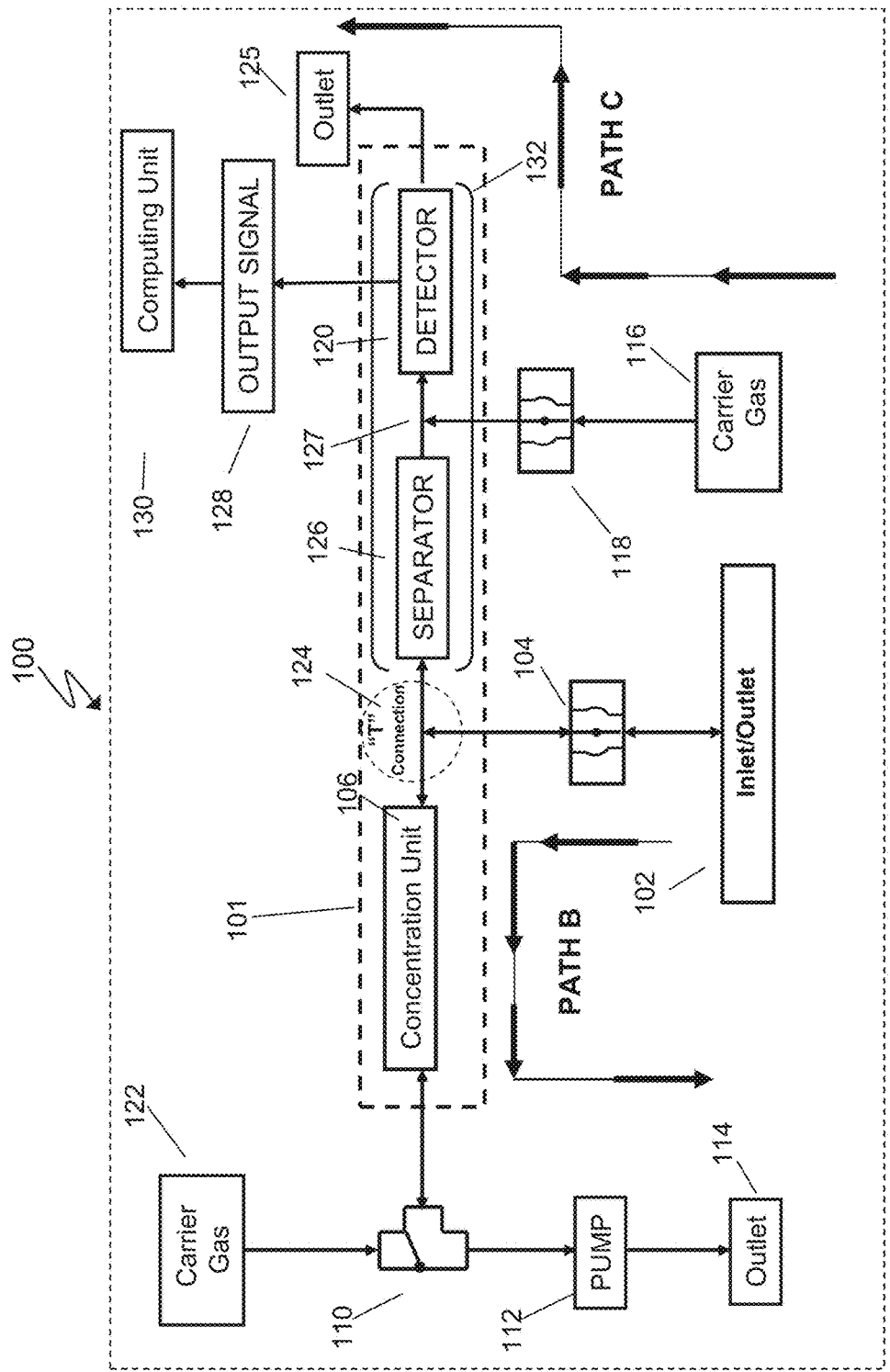
FIG. 5 is a schematic illustration of the apparatus of FIG. 2 wherein inert gas is streamed from a utility/carrier gas source toward a detection unit and a gas sample is streamed via a concentration unit toward an outlet, according to some embodiments of the present invention.

A passage 99, optionally valveless, with a relatively smooth inner wall connects between the detector 120 and the concentrating element of the concentrating unit 106, optionally via the chromatographic separator 126. Optionally, the external diameter of the passage, and optionally of other passages along paths A-D in FIGS. 4-6 is about 1 mm. The diameter of the lumen of the passage is about 0.8 mm diameter.

In such a manner, there are no regions with absorptive surfaces that append and discharge analytes back into a lumen between the concentrating element of the concentrating unit 106 and the detector 120. In addition, as no valves are used, less or no contamination spots are formed. Further, no cold spots remain during the heating of the analysis apparatus 100. The streaming of gas along the passage 99 between the chromatographic separator 126 and the concentrating element of the concentrating unit 106 increases the response time of the analysis apparatus 100 and therefore improves the operational throughput thereof. Optionally, the connection between the concentration unit 106 and the detector 120 is performed via a T shaped tubular element 124 that does not include contaminable valves or projections. Optionally, the T shaped tubular element 124 have straight inner wall that is optionally coated with a hermetic layer of a material that does not absorb or interact with the analytes which are inspected by the analysis apparatus 100.

As depicted in FIG. 1, the aperture 102 is connected to the passage 99, between the detector 120 and the concentrating element of the concentrating unit 106. Opposing paths may pass through the concentrating element of the concentrating unit 106, for example as shown at 81 and 90. For example, a pump 112 which is positioned in one side of the concentrating unit 106, may draw a gas sample from the aperture 102 via the concentration unit 106, for example as described below and shown at 80. For clarity, the gas sample may include vapors of various components, dust, and/or airborne solid and liquid particulates. It should be noted that any other mechanical device that moves gas by pressure or suction may be used instead of the pump 112. In addition, a gas source 122, which is positioned at the same side as the pump 112, may stream a carrier gas and/or utility gas, such as inert gas, via the concentration unit 106, toward the detector 120 and the chromatographic separator 126, for example as described below and shown at 81. Optionally, the gas which is streamed in the lumens of the apparatus 100 is about 10 pounds per square inch (PSI). Optionally, the carrier gas source 122 comprises one or more gas containers.

Optionally, the carrier gas is an inert gas, such as HE gas. In such a manner, one path 80 may be used for bonding analytes on the concentrating element of the concentrating unit 106 while another 81 is used for transferring the analytes which are discharged from the concentrating element of the concentrating unit 106 toward the detector 120, optionally via the chromatographic separator 126. As a number of paths are passing via the passage 99, the total length of the analysis apparatus 100 may be reduced.

According to some embodiments of the present invention, the analysis apparatus 100 may be used for detecting one or more groups of compounds, for example explosives, by analyzing vapors which are drawn with the gas sample. In such an embodiment, a concentration element that is adapted to bond the one or more groups of compounds which may be selected, for example a platinum coil for explosives. Additionally or alternatively, the chromatographic separator may be adjusted for the one or more groups of compounds, for example packed with CG column packed with Silicon OV 275 and supported on Chromosorb® 80-100 mesh for explosives as described below. In such embodiments, as the chromatographic separator 126 and/or the concentration element are adapted to a limited number of components, the size of the analysis apparatus 100 may be limited, for example few dozens of centimeters as described below and depicted in FIGS. 9A-9E. Such a limited size allows using the apparatus as a handheld device. It should be noted that as the chromatographic separator 126 and/or the concentration element are adapted to a limited number of components, the heating temperature range may be limited to a relatively narrow range. Furthermore, as exemplify below, the period of each analysis cycle may be reduced to about 6-20 seconds and the energy that is required per analysis cycle is respectively reduced.

Figure 2:
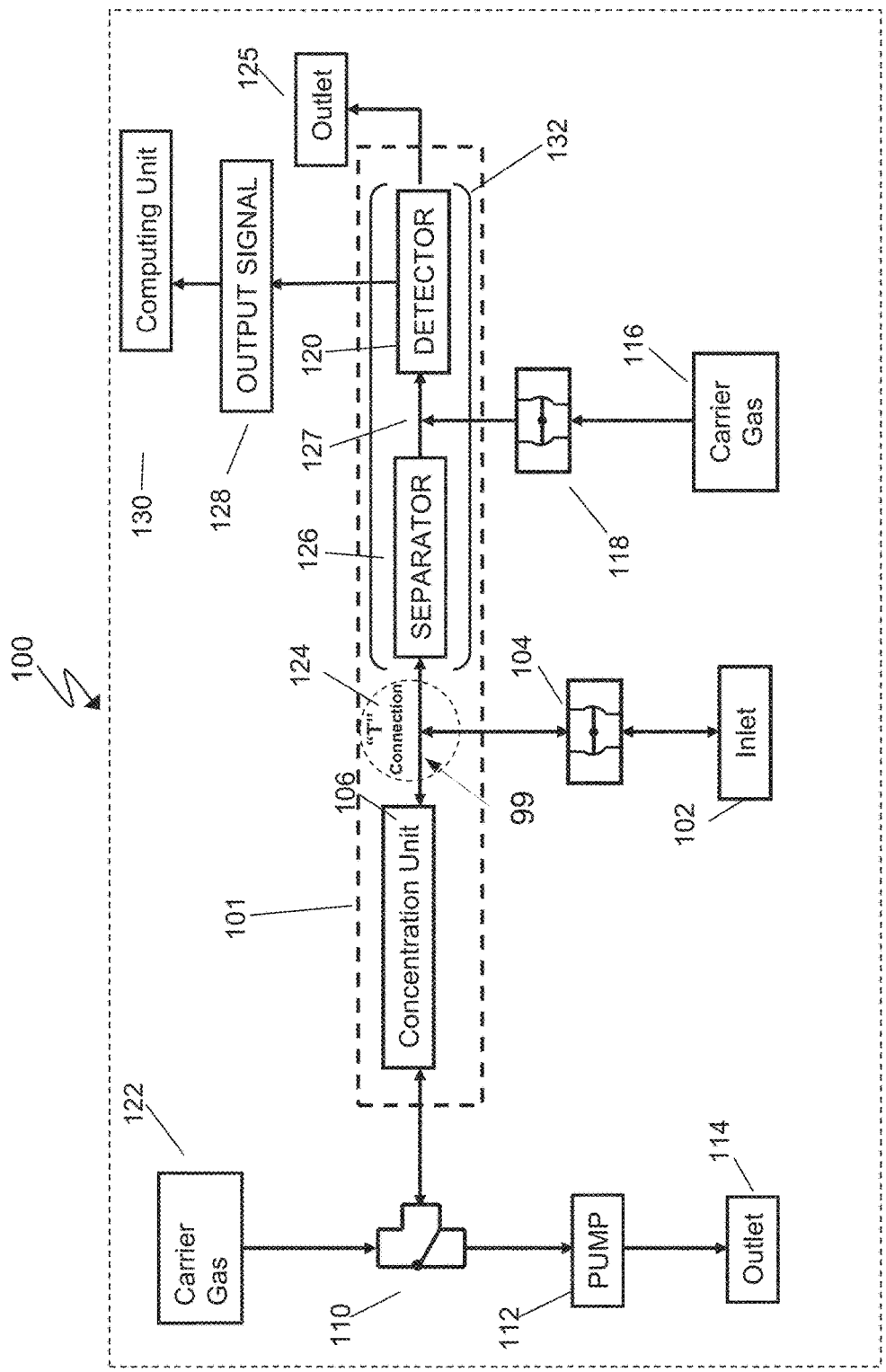
FIG. 2 is another schematic illustration of an apparatus for detecting a presence of a chemical substance, according to some embodiments of the present invention.

Reference is now also made to FIG. 2, which is a schematic illustration of the analysis apparatus 100, according to some embodiments of the present invention. The concentrating element of the concentrating unit 106, the detector 120, the chromatographic separator 126, the passage 99 and the aperture 102 are as described above; however FIG. 2 further depicts a number of components pertaining to some embodiments of the present invention. As depicted in FIG. 2, the apparatus includes a heating element 132, such as a heating chamber, that confines the detector 120 and the chromatographic separator 126.

According to some embodiments of the present invention, the chromatographic separator 126 may be packed with Silicon OV 275, also known as dicyanoallyl, supported on Chromosorb® 80-100 mesh. Optionally, the concentration of the Silicon OV 275 is between 3% and 10%, for example 5%. It should be noted that the chromatographic separator 126 may be packed with other material, for example OV 225 and/or other silicone materials. The travel of the gas stream through the chromatographic separator 126 may last approximately between 4 seconds and 25 seconds. As described above, the chromatographic separator 126 may be heated while in standby and operative modes. Optionally, the chromatographic separator 126 is heated to 130°, or to approximately 130°.

The detector 120 has an outlet 125 for extracting the gas that is streamed therethrough, for example as described below.

Optionally, the concentrating element of the concentrating unit 106 is connected, optionally via a gas path switching element 110, such as a T shaped three ways valve, to the gas source 122 which is used for releasing carrier gas and optionally utility gas. The carrier gas source 122 may include any inert gas, such as Helium (He) gas, Neon (Ne) gas, Argon (Ar) gas, and the like. In such an embodiment, the concentrating element of the concentrating unit 106 is also connected, via the path switching element 110, to the pump 112 that draws gas therefrom when activated.

Figure 3:
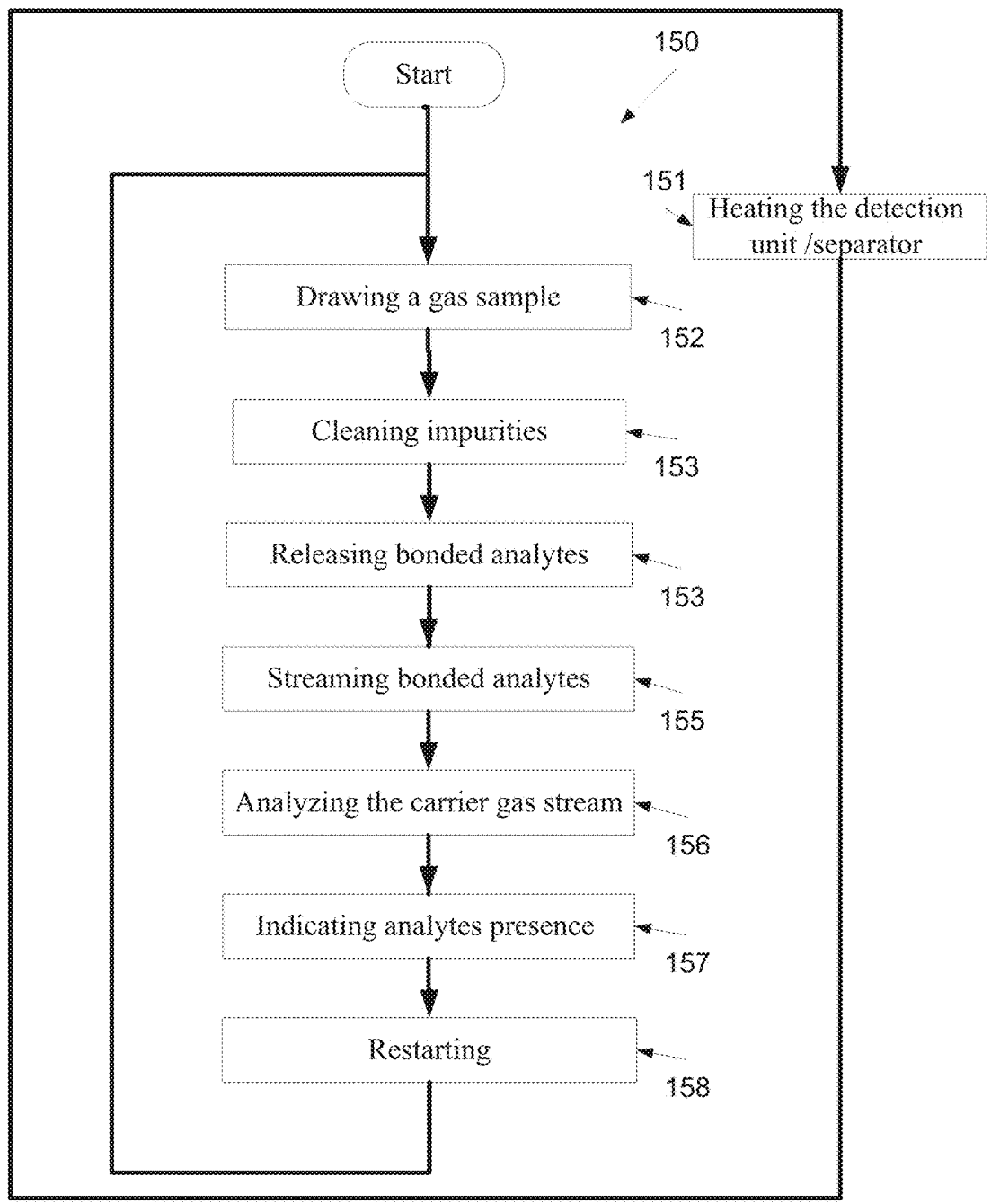
FIG. 3 is a flowchart of a method for inspecting one or more analytes in a gas sample, according to some embodiments of the present invention.

Reference is now also made to FIG. 3, which is a flowchart of a method 150 for inspecting one or more analytes in a gas sample, according to some embodiments of the present invention. For clarity, blocks 151-158, in the flow order depicted in FIG. 3, describes an exemplary detection cycle. As described below, each detection cycle may last for a period of between 6 and 20 seconds and may be repeated every 10-30 seconds.

In use, as shown at 151, the detector 120 is initialized by elevating the temperature thereof. This heating may be maintained during both an operational mode, during which the detection cycle is performed, and while the analysis apparatus 100 is in a standby mode. In such a manner, the analysis apparatus 100 may switch from a standby mode to an operational mode for inspecting a gas sample within less than 5 seconds, for example, within less than 2 seconds. Optionally, the temperature of the one or more chemical detectors and/or a target space in front or within the chemical detectors is increased to between 100° and 150°, optionally between 120° and 135°. It should be noted that as the apparatus may be adapted to selected molecules, for example explosive the temperature range may be limited. Such a limited range allows fast heating and cooling, for example as described above.

Optionally, the chromatographic separator 126 is simultaneously heated, optionally, by the same heating element. Optionally, the chromatographic separator 126 is a CG column. In such an embodiment, the heating may be performed by a column oven, such as an insulated box sized and shaped to allow comfortable installation of the column and optionally the detector 120. The column oven may be heated by electrical heating elements arranged around a circulatory fan. Sensors may be used to maintain a stable isothermal temperature and to control the initial temperature lag.

According to some embodiments of the present invention, gas is streamed from the gas source 122 toward the outlet 125, via the chromatographic separator 126 and the detector 120, when the apparatus is in a standby mode. The path of the gas is shown by path A in FIG. 4. As described above, the chromatographic separator 126 and the detector 120 are heated during the standby mode. The flow of the inert gas along path A induces gas turnover in around the chromatographic separator 126 and the detector 120. In such a manner, the chemical detector may not be overheated and/or maintained at a working temperature which is identical, or substantially identical to its temperature when a carrier gas is streamed, for example as described below. Optionally, the temperature is maintained for a period of 10 minutes or more, for example 30 minutes, 45 minutes, 1 hour, 2 hours, 10 hours, 24 hours, and any intermediate or longer period. This period may be referred to herein as a standby period.

As shown at 152, a gas sample stream is drawn via the concentration unit 106 so that one or more analytes from the gas sample are bonded thereto. Optionally, the gas sample stream is drawn by the pump, for example along path B that is depicted in FIG. 5. As shown at FIG. 5 the gas sample stream, which is optionally drawn from ambient air in proximity to the aperture 102, passes through a valve 104, such as a two-way valve. The valve is opened according to instructions from a central controller and/or by the drawing force that is applied by the pump 114. The gas sample stream is drawn via the concentration unit 106 and the optional gas path switching element 110 and released to the atmosphere via the outlet 114.

Optionally, the suction that is applied by pump 112 draws the gas sample via the concentration unit 106, which is optionally a preconcentrator, during a period that allows a collection of analytes. The collection period may last as long as needed; for example, depend of the type of the probed analytes and/or according to instruction from the operator of the analysis apparatus 100. For example, the analysis apparatus 100 may be housed in a handheld device, allowing the operator to maneuver the analysis apparatus 100 along the clothing of a suspect and/or the perimeter of a probed article. The collection period may last while the operator maneuvers the apparatus along the suspect and/or the article. During the collection period, the concentration unit 106 adsorbs the analysts. For example, the concentration unit 106 includes a chamber that houses a platinum coil that has a strong affinity to adsorb analysts such as explosive molecules from the polar groups. The exiting air stream passes through valve 104 and is pumped out by pump 106. Optionally, the coil has a diameter of about 0.5 mm, and between 18 and 40 turns (or even more), optionally 30, for example as depicted in FIGS. 6A-6C. It should be noted that the higher is number of turns, the higher is the ability of the platinum coil to adsorb analysts. Therefore, more turns improve the sensitivity of the analysis apparatus 100. As described above, the coil is placed in a chamber. An exemplary chamber and the sizes thereof are provided in FIGS. 7A-7D. As depicted in FIG. 7A, the chamber 160 has two apertures 162 that allows placing the coil therein and connecting the coil to an external heating element for facilitating the heating thereof, for example as described below. Optionally, as shown the chamber includes an aperture that functions as the inlet/outlet 102. As the aperture is carved in the chamber 160, no screws, rivets, and/or adhering points are needed. In such a manner, areas for potential accumulation of infections and/or compounds which may divert the detection process are avoided.

Optionally, a flow of utility gas is maintained via the detector 120 while the gas sample is drawn via the concentration unit 106, shown at 152. As the gas sample is drawn, the gas path switching element 110 changes the path of gas that passes therethrough. The stream of inert gas from the utility/carrier gas source 122 is either occluded or diverted from the concentration unit 106, for example as shown at FIG. 5. In such a manner, the inert gas does not impinge, dilute, and/or tabulate the gas sample stream. In such an embodiment, and in order to maintain a flow of gas via the detector 120 while the gas sample is drawn via the concentration unit 106, the apparatus further comprises an additional utility gas source 116 that provides a gas stream along the heated detector 120. For example, as shown by path C at FIGS. 5 and 6, the additional utility gas source 116 releases inert gas that flows toward the outlet 125, via the detector 120. In such a manner, a gas flow is maintained in the detector 120 during the collection period. Optionally, a valve 118, such as a two ways valve is, positioned between the additional utility gas source 116 and the detector 120. The valve 118 is optionally controlled by the controller (not shown) of the analysis apparatus 100 and/or by the flow of gas from the additional utility gas source 116. It should be noted that this gas flow removes analytes which may have been left in the proximity of the detector 120 from previous inspections. Furthermore, in such a manner the reading of detector 120 remains steady when the gas sample is drawn, with a steady base line that is not affected by the occlusion and/or diversion of the flow of gas from the utility/carrier gas source 122.

During the drawing of the gas sample, the chromatographic separator 126 separates between the gas sample that flows along path B and the inert gas that flows along path C. Optionally, the separation is induced from a pressure difference in lumens of the apparatus. For example, the pressure difference between the lumens that bound the chromatographic separator 126 from its sides. This pressure difference is created by the density of the CG column and/or the gas membrane of the chromatographic separator 126.

Optionally, as shown at 153, impurities and reminders of chemicals are removed from the concentration unit 106 and the passages which are placed between the gas sample inlet and the carrier gas are washed out. Optionally, the carrier gas source 122 streams gas that passes through the concentration element toward the inlet/outlet 102, path D in FIG. 8 passes. This process is useful in order to ensure that compounds which may have been drawn during the concentration period and left in the passages of the analysis apparatus 100 are removed and therefore do not effect the readings of chemical detector 120. It should be noted that taught some of the analytes which are bonded to the concentration element may be washed out, enough remain to be detected the chemical detector. Similarly to the described above, the density of the chromatographic separator 126 ensures that impurities are streamed via the inlet/outlet 102 and not via the detector 120. Optionally, the gas is streamed for a period of less than one second, for example, 0.25 second. The passages may be purified in such a short period as the length of path D is only several centimeters long.

It should be noted that the extracting of impurities and reminders before the streaming of the analytes toward the detector 120 reduces the prevalence of false alarms. Such a reduction may even be intensified when the chromatographic separator 126 and/or the concentration element are adapted to bond with a selected group of compounds, for example as described above.

Now, as shown at 154, after the gas sample is drawn from the ambient air and the impurities are optionally removed, the concentrated analytes are released from the in concentration unit 106. Optionally, the releasing is performed by increasing the temperature of the concentration element, for example the platinum coil, optionally to 200° C. or more, for instance to about 220° C., for instance by passing an electrical current therethrough. It should be noted that as the release is performed in relatively low temperature, less analytes are burnt. Moreover, such a relatively low temperature allows using less energy in each detection cycle. The heating enables desorption of the bonded analytes from the concentration element so as to allow the absorption thereof into carrier gas stream. Optionally, the heating a concentration element, such as a platinum coil, is performed in less than 2 seconds, for example about 1.2 seconds.

Now, as shown at 155, after the temperature of the concentration element is increased for a predefined period and/or to predefined temperature, carrier gas is streamed via the concentration unit 106 so as to carry the released analytes toward the chemical detector 120, optionally via the chromatographic separator 126, for example as depicted in path A in FIG. 4. Optionally, this stage lasts for a period of between about 6 and about 20 seconds. This period may vary to correspond with the operation of different chemical detectors which may be used. The period may be adjusted by a controller that controls the valves 110, 104, 118 and/or the gas sources 116, 122, optionally according to user's instructions, optionally received using an MMI and/or dynamically according to a change that is detected by temperature and/or flow detectors in the concentration unit 106.

The streaming of the inert gas via the concentration unit 106 conveys analytes which are released, if released, from the concentration element to the area that is probed by the chemical detectors of the detector 120. The analytes carried by carrier gas may comprise particles, vapors, or gas molecules that have been thermally desorbed, disband and/or otherwise released from the concentration unit 106 when heated to an elevated temperature.

As shown at 156, the detector 120, for example with the chemical detectors, is employed for analyzing the flow of carrier gas. The output of the chemical detectors is forwarded, optionally via a commonly used signal processor 128, to an internal and/or external computing unit. The computing unit 130 may be integrated into the apparatus or connected thereto via a wired and/or a wireless connection. An external computing unit 130 may be a client terminal, such as a laptop, a personal digital assistant (PDA), a Smartphone, and/or any other computing unit 130.

Optionally, the computing unit 130 analyzes the received signals and generates accordingly an alarm and/or any indication of analytes presence, absence, amount and/or concentration, as shown at 157. In such an embodiment, the computing unit 130 is connected to a an alarm indication means, such as one or more light emitting diodes (LEDs), alarm horn or buzzer, vibrator and the like, to allow indication of an alarm situation to the user. Optionally, the alarm and/or the analytes presence indication are forwarded via a wired and/or a wireless means, such as a common Bluetooth™ or Wi-Fi™ interface, to a remote management unit. Such a management unit may react to the alarm and/or the analytes presence indication, for example by operating a self defense system and/or by notifying one or more predefined agents.

Optionally, the computing unit 130 is designed to receive the outputs of the detection unit and/or control the valves of the apparatus. Optionally, the computing unit 130 stores the outputs of the detection unit is a storage unit which is connected thereto. Optionally, the computing unit 130 is connected to a men machine interface (MMI), such as a keyboard, a keypad, a touch screen, and the like (not shown) to allow entering commands to the analysis apparatus 100.

The computing unit 130 supports the processing of the signals which are received from the output signal unit 128 and analyzing it, for example by comparing it to one or more reference values or graphs, for example as described below.

As shown at 158, after the released analytes have been transported toward the detection unit 106 and analyzed the apparatus is restarted. For example, about 1.25 seconds after the heating of the concentration element, a cooling period of approximately 4 seconds is initiated. The cooling is optionally performed by streaming the gas via the concentration element. The concentration element, which is optionally a platinum, may be cooled to about the room temperature, for example by stopping the electrical current that has been passed therethrough. The cooling of the platinum coil or tungsten coil may be aided by the flow of the inert gas from the utility/carrier gas source.

Figure 8:
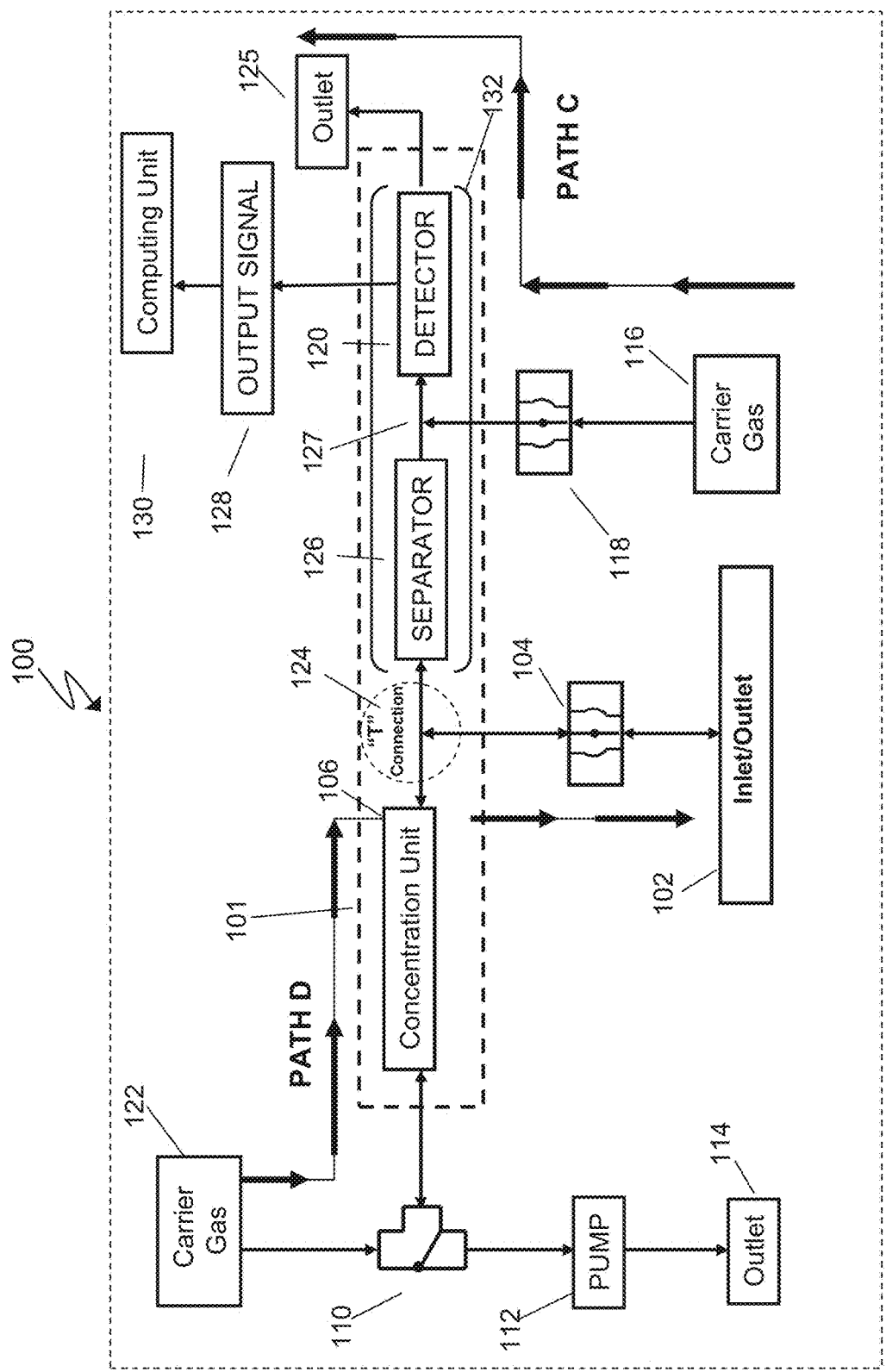
FIG. 8 is a schematic illustration of the apparatus of FIG. 2 wherein inert gas is streamed from a utility/carrier gas source via a concentration unit toward an aperture and from an additional utility gas source via the detection unit toward an outlet, according to some embodiments of the present invention.

Additionally or alternatively, the restarting may include purifying the lumens of the analysis apparatus 100 after the detection unit has analyzed the analytes in the carrier gas. The purification may be performed by streaming the gas from the utility/carrier gas sources 122, 116, for example as shown by paths C and D which are depicted in FIG. 8 and/or path A in FIG. 4. After a defined period of time, for example of between 2 and 10 seconds, for example 4 seconds, a major portion of the remaining of the molecules in the concentration unit 106 is assumed to be washed outside analysis apparatus 100. The valves 104, and 118 and the gas path switching element 110 are optionally adjusted to allow the flow of gas along the selected paths. Additionally or alternatively, the temperature of the concentration element and/or the detector, and optionally the separator, is raised for burning analytes and/or gas sample residuals.

Optionally, such a purifying is performed when the apparatus is inoperative for a certain period and/or periodically. This process may be useful in order to ensure that residuals of the gas which may have been left in the lumens of the analysis apparatus 100. Furthermore, by cleaning the lumens of the apparatus false detection of chemical substances and compounds may be avoided. The analytes, which are bonded to the concentration element, are gathered from the gas sample that is drawn in the respective detection cycle and analytes gathered from previous detection cycles are washed away with the cleaning stream.

Additionally or alternatively, the temperature of chromatographic separator 126 and detector 120 may be increased to about 200° C. for burning residuals which may have been left in the analysis apparatus 100.

Optionally, as shown at 158, the inspection process that is depicted in 152-158 is repeated, either automatically, for example every 10-30 seconds, every minute, every five minutes, and every ten minutes and/or any intermediate or longer period or manually, according to instructions received from the user. Optionally, the apparatus may synchronized for inspecting articles which are moving in a certain pace, for example in a production line, for instance by a convening belt. The ability to perform an inspection cycle every 10-30 seconds allows using the apparatus for inspecting a line of suspects and/or a group of articles with a relatively high throughput. It should be noted that the apparatus may be operated automatically, for example according to the outputs of a moving sensor, or manually, for instance based on inputs of a user. The apparatus may be operated substantially continually, with maintenance, such as gas source refill interludes.

It should be noted that the length of the period during which each one of the aforementioned streams are released may depend upon operating conditions such as the working temperature of the detector 120 and the chromatographic separator 126, the gas flow rate, the characteristics of the analytes and/or characteristics of the molecules of the gas sample, such as size and polarity.

The operating temperature in chromatographic separator 126, as well as the flow rate therealong, may be set based on characteristics of the specific compounds or substances to be analyzed and/or the design and materials of a packed column thereof. In the case where the detected molecules are of explosives, chromatographic separator 126 may be operated under a substantially steady temperature ranging from 120° C. to 130° C. and a substantially constant flow rate of the inert gas carrying the molecules. Thus, the temperature of chromatographic separator 126 and detector 120 may be kept in the range of 120° C.-140° C. by heating means 132 throughout the entire period of operating of analysis apparatus 100.

Figure 9C:
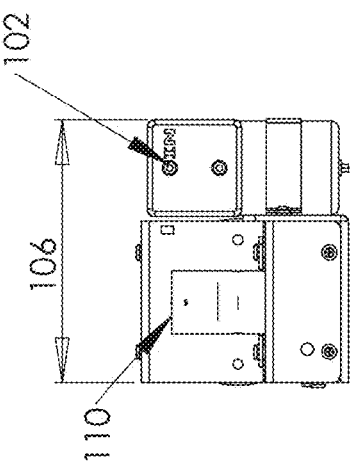
FIGS. 9A-9E are schematic illustration of an exemplary detection apparatus and the sizes thereof, according to some embodiments of the present invention.
Figure 9B:
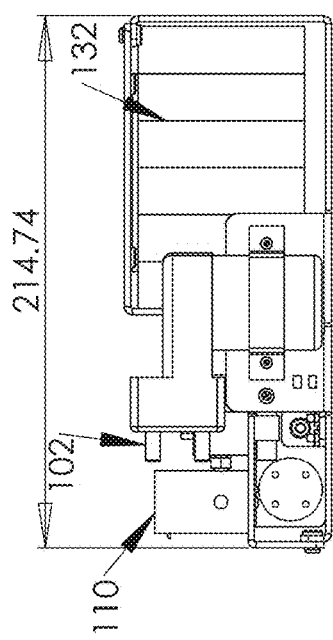
Figure 9D:
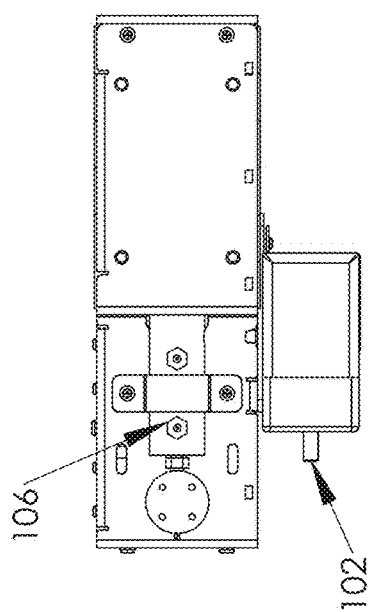
Figure 9A:
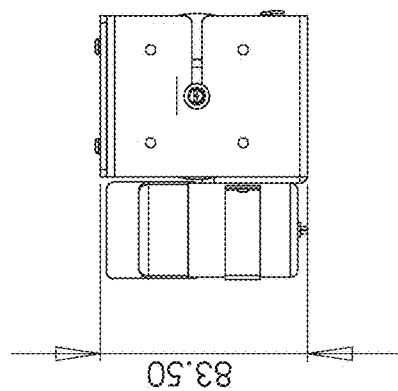
Figure 9E:
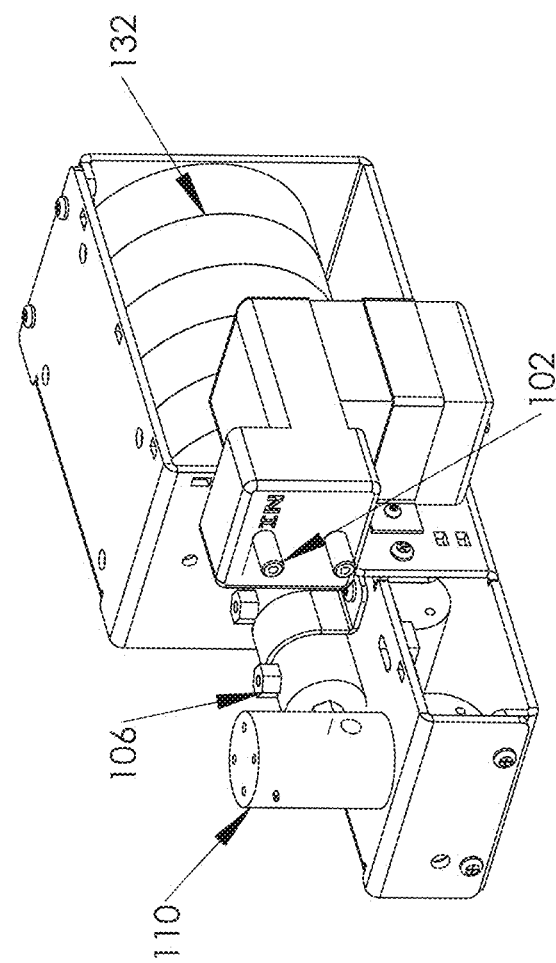

Optionally, the analysis apparatus 100 is housed in a housing that is sized and shaped to be carried by a user, for example as a wand shaped device. FIGS. 9A-9E respectively depicts rear, lateral, frontal, top, and general illustrations arrangement of the analysis apparatus 100, according to some embodiments of the present invention. FIGS. 9A-7C exemplify the limited dimensions of the apparatus, in centimeters, As outlined above, the concentration unit 106 comprises a concentration element, such as a coil or a porous element, which is shaped to collect the analytes. Optionally, the concentration unit 106 includes a chamber, which may be referred to as a lumen, equipped with a platinum coil. Optionally, the diameter of the lumen is between 4 mm and 8 mm, for example 6 mm.

When the gas sample is drawn through the concentration unit 106 it passes in the chamber, crossing the surface of the platinum coil. In such a manner, some or all of the analytes in the gas sample are bonded to the concentration unit 106. It should be noted the analytes such as molecules of explosives typically contain an uneven distribution of electrons that enables it to take part in electrostatic interactions. Therefore, such molecules have a strong affinity to adsorb onto metallic materials such as platinum.

According to some embodiments of the present invention, the concentration unit 106 includes a metallic element that is coated with a layer of substance or a compound having a high adsorbing coefficient. Optionally, the layer comprises a silicone polymer with methyl phenyl silicones. Optionally, the layer comprises OV-17 (phenyl methyl, 50% phenyl). Optionally, the OV-17 is dissolved with acetone to a concentration of between 3% and 10%, optionally, a concentration of 5%. The metallic element is now coated with the dissolved solution. Such a concentration rate assures that the amount of analytes that is collected by the concentration unit 106 is sufficient for the detection thereof by the detector 120. At the same time, the concentration rate allows the releasing of the analytes from the concentration unit 106 by heating the metallic element, for example as described below.

It should be notes that the above embodiment is based on a surprising discovery of that a metallic element which is coated with a layer of OV-17 with a concentration of about 5% improves the bonding of molecules of analytes such as explosives. It should be noted that different concentrations have different bonding levels for different analytes.

As described above, the detection unit 106 may use reference values for detecting a presence of exemplary analytes, for example molecules of an explosive. Optionally, the reference values include one or more graphs of an estimated reaction of a certain chemical detector to the presences of one or more analytes during a detection cycle. By comparing between the reference values and the actual outputs of the certain chemical detector, the presence of the one or more analytes may be estimated.

Figure 10A:
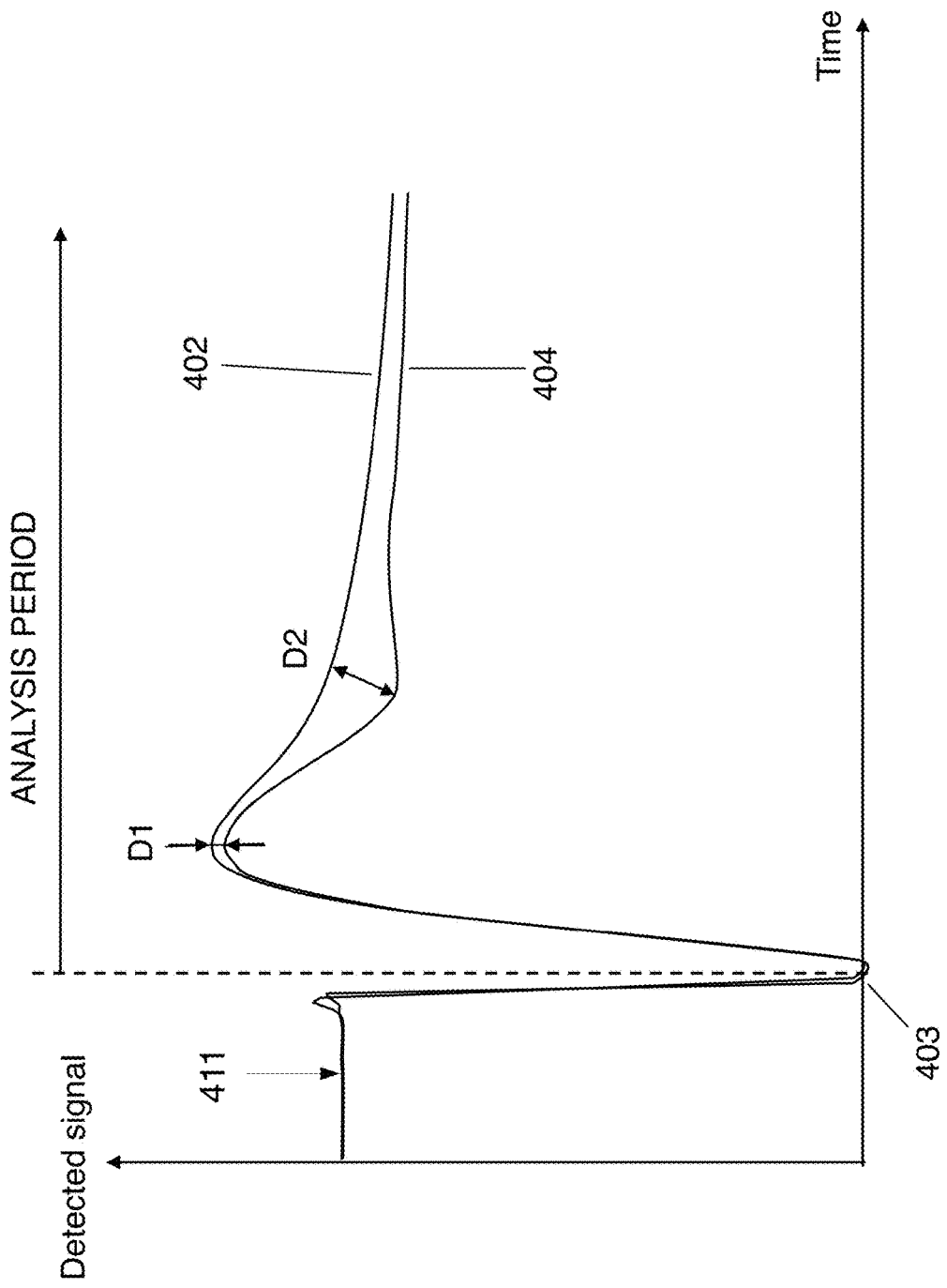
FIGS. 10A-10D are graphs presenting an exemplary curve of reference values and a curve of an exemplary signal received from a chemical detector during an exemplary detection cycle, according to some embodiments of the present invention.

Reference is made now to FIG. 10A, which is a graph presenting an exemplary curve 402 of reference values and a curve 404 of an exemplary signal received from a chemical detector 153 during an exemplary detection cycle, according to some embodiments of the present invention. The graph is acquired by using the apparatus depicted in FIGS. 4-9E and described above. As depicted in FIG. 10A, exemplary graphs 402 and 404 are partly overlapping where the deviation between them, denoted herein by D1 and D2, may be indicative to the presence, the absence and/or a centricity detection level of the one or more analytes.

The exemplary reference curve 402 represents an optional detection cycle having a number of phases. During the first phase, marked with the numeral 411, the device collects the analytes from a gas sample. As described above, a utility gas is streamed to maintain the temperature of and/or in proximity to the chemical detector. The steep decline which follows the first phase is an outcome of an intermediate period during which the carrier gas that is streamed toward the chemical detector, for example as depicted in 155 and by path A in FIG. 4, replaces the utility gas that is streamed during the concentration period and by path C in FIG. 8. During this intermediate phase, the lumens are purified. After the purifying is completed, the analytes are released and transferred toward the detector 120 in a measurement phase. The signal pitch of the exemplary curve 402 is based on the expected output of one or more of the chemical detectors during these phases. For example, the intermediate phase is expected to produce a relatively short and steep decline of the signal pitch and the measurement phase is expected to produce relatively short and steep incline of the signal pitch as an outcome of the detection of the one or more analytes. An exemplary occurrence of the event between the purifying and the measurement event is marked by a vertical dashed line crossing through point 403. The incline is expected to be followed with a milder decline, which is indicative of the return of the chemical detector's reading to a normal standby level. In use, the signal received from chemical detector of the detector 120 is compared with the stored reference signal, such as signal corresponding to curve 402. The curves 402, 404 are optionally superimposed so that a deviation between them may be detected. The deviation may last from few tenths or hundredths of a second from a reference point, such as 403, depending on the nature of the one or more probed analytes. It should be understood that the deviation between two curves may consider many parameters and the indication of differences, such as differences D1 and D2 at certain points does not necessarily limits the scope of the analysis of the deviation.

Figure 10B:
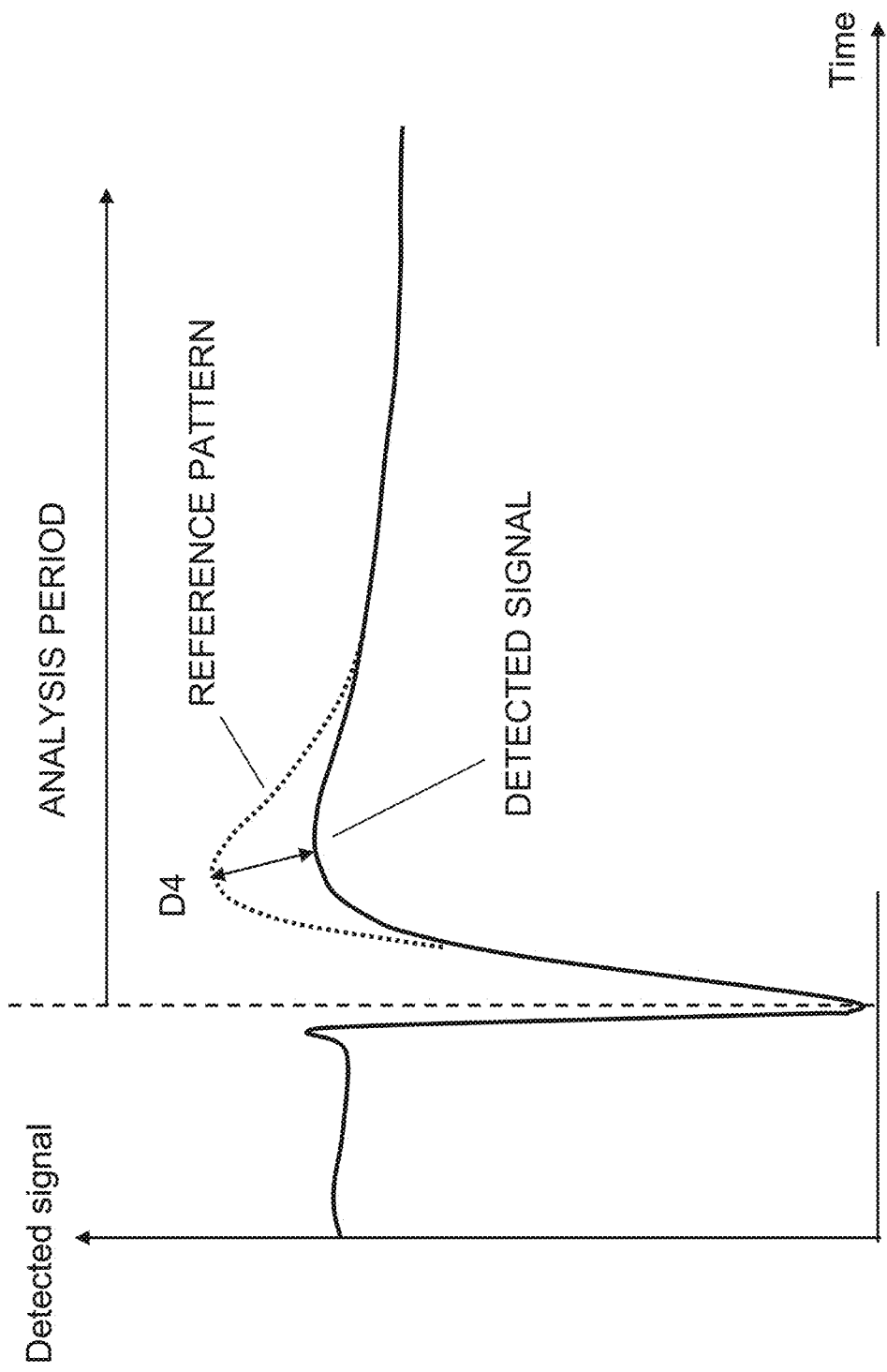
Figure 10C:
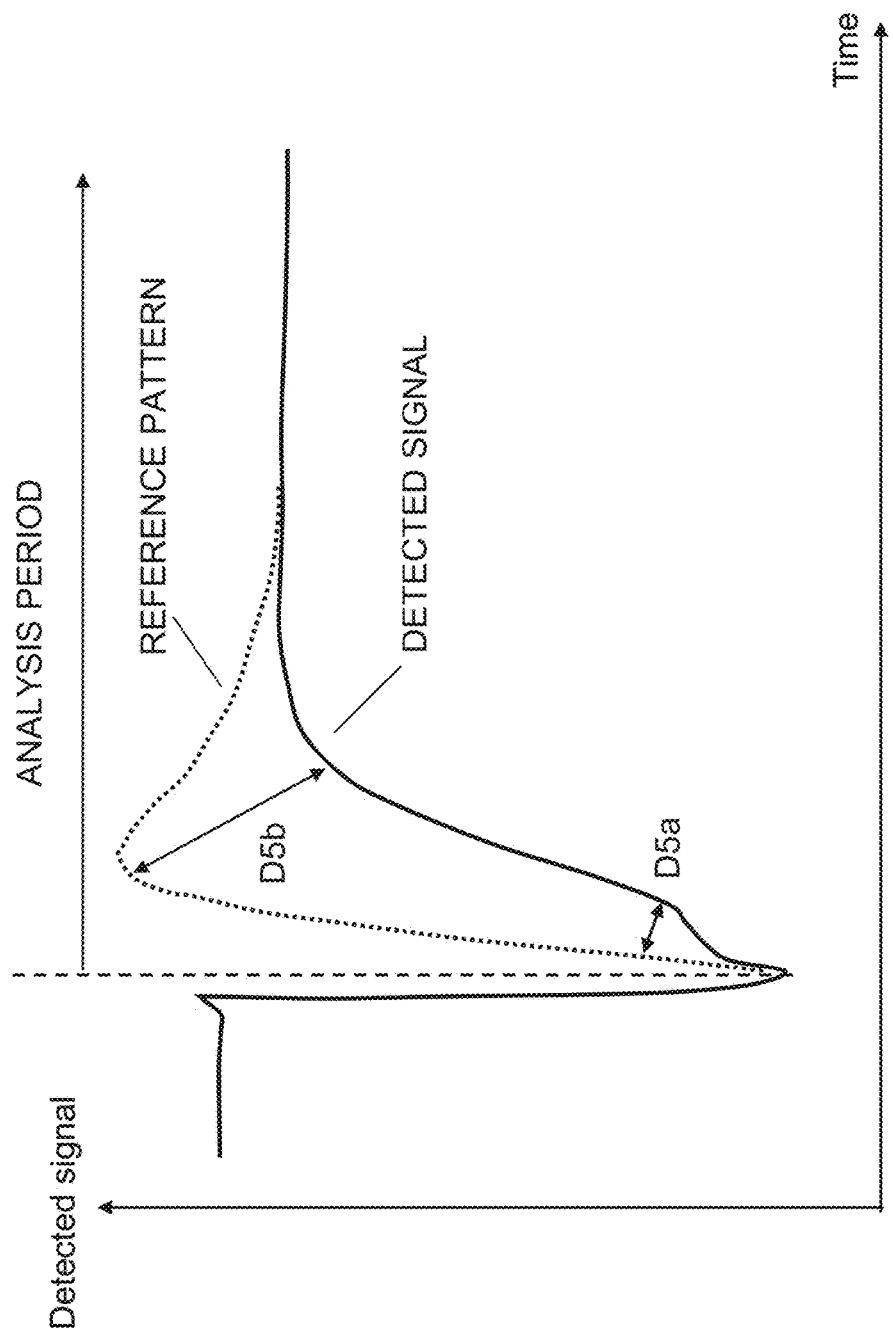
Figure 10D:
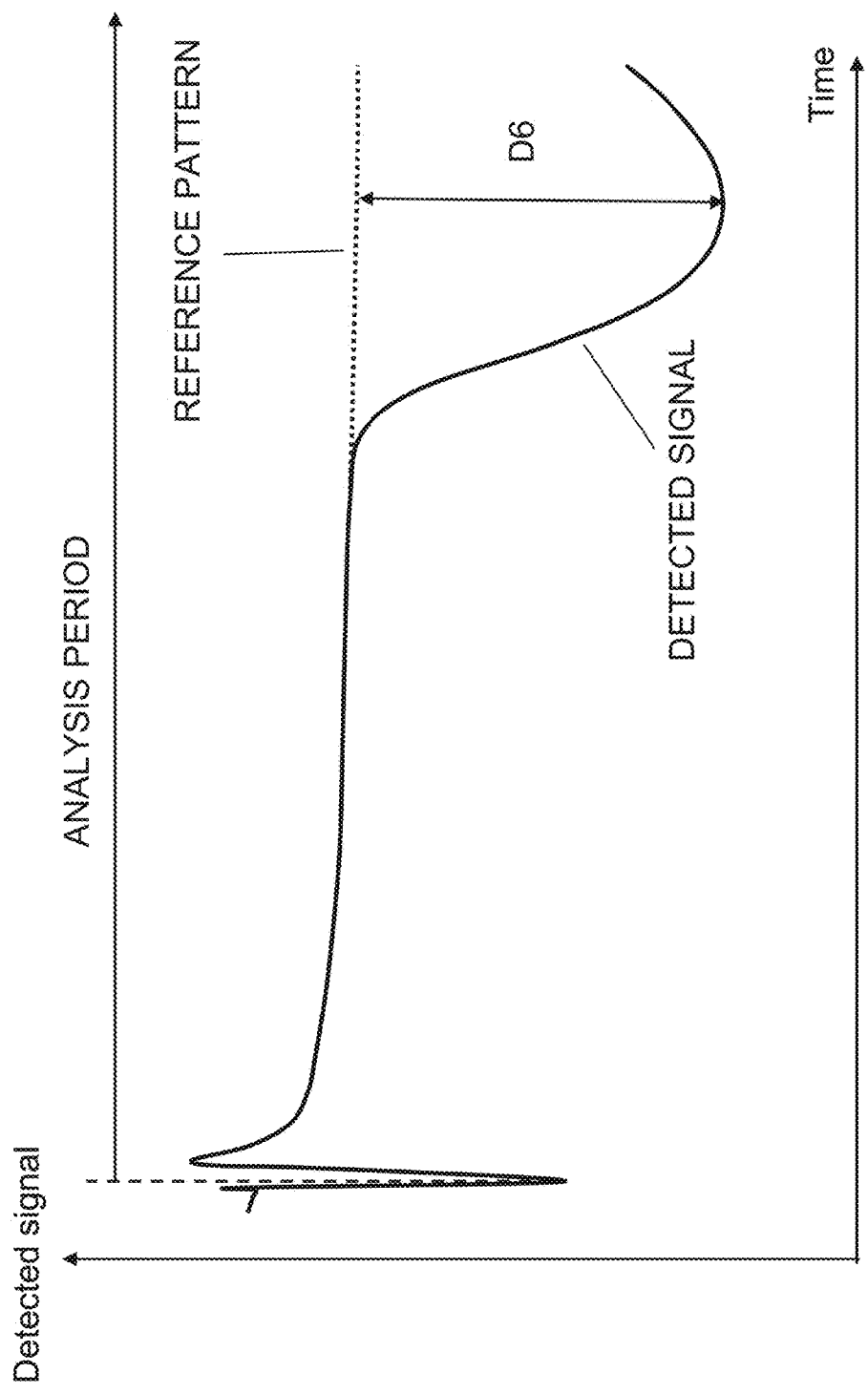
Figure 11B:
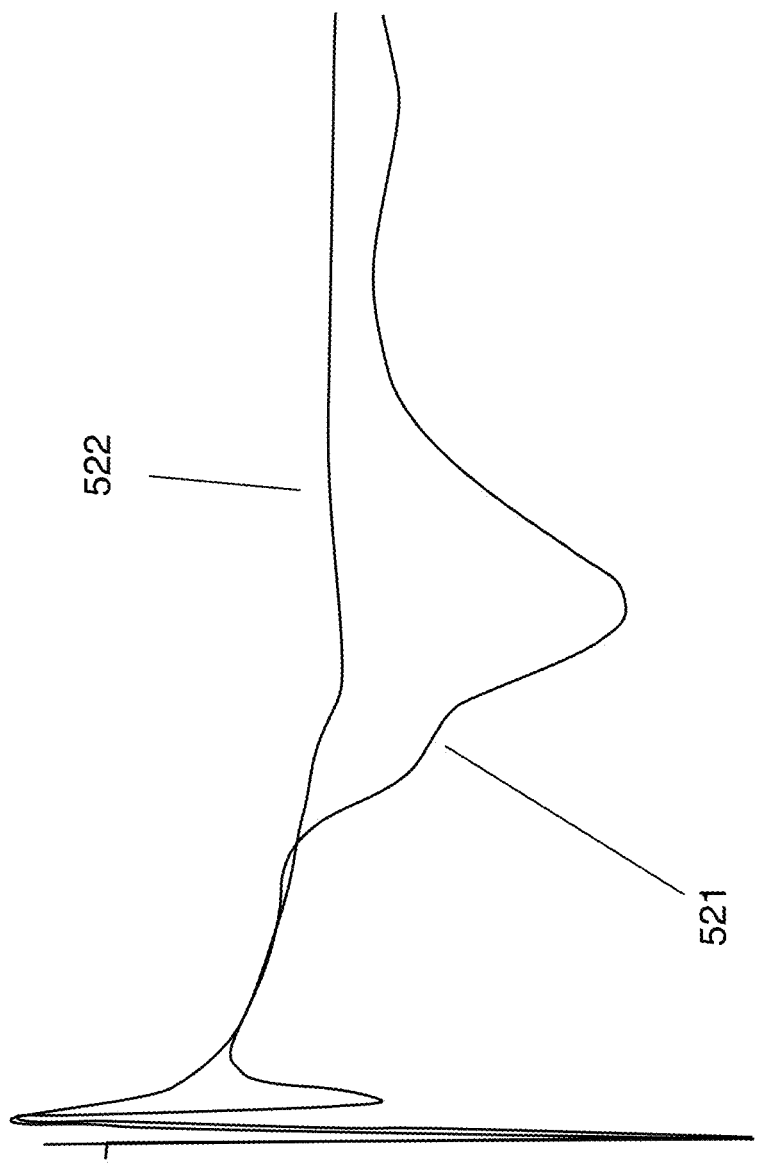
Figure 11C:
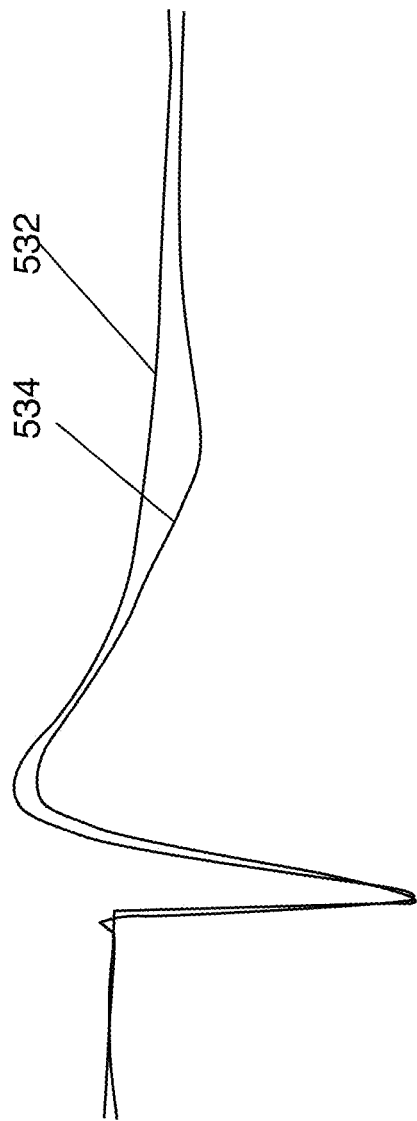
Figure 11D:
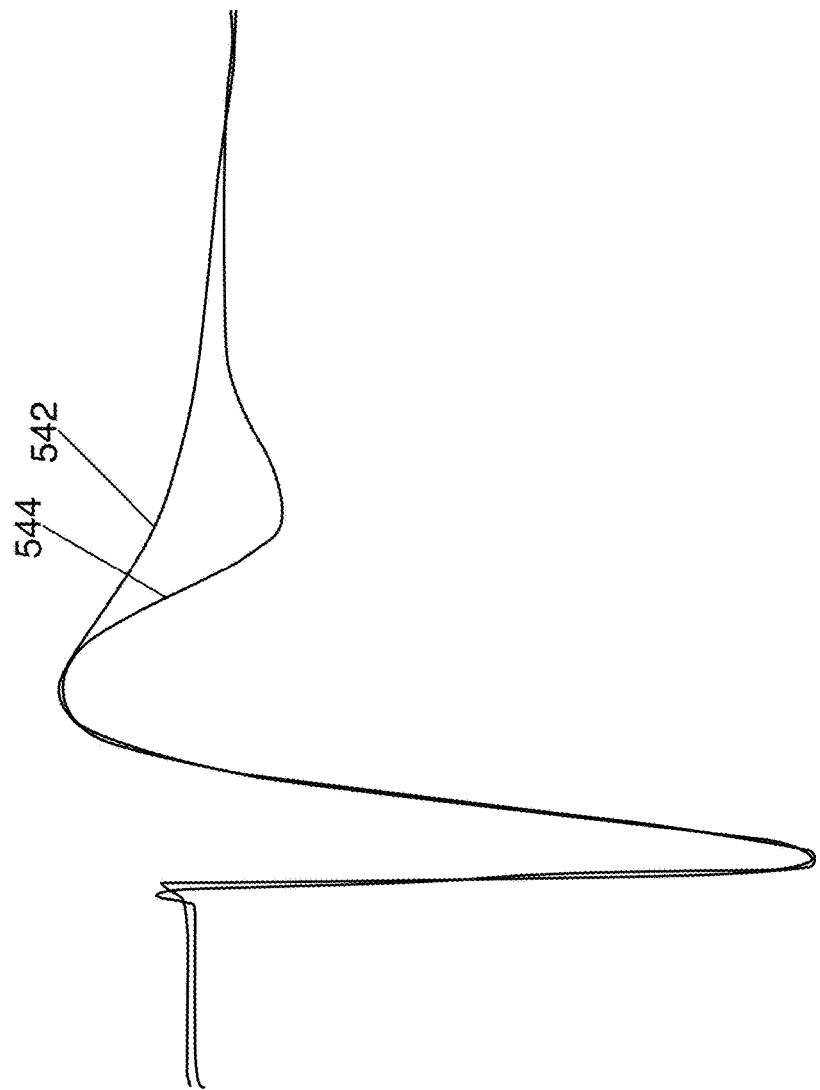
Figure 11E:
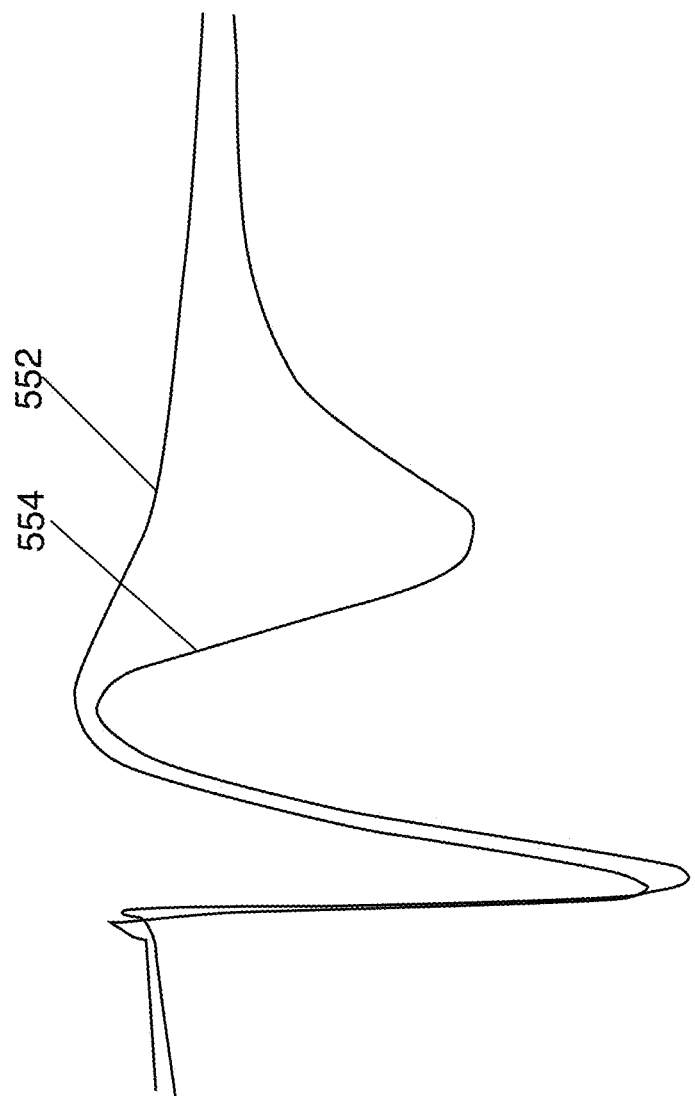
Figure 11F:
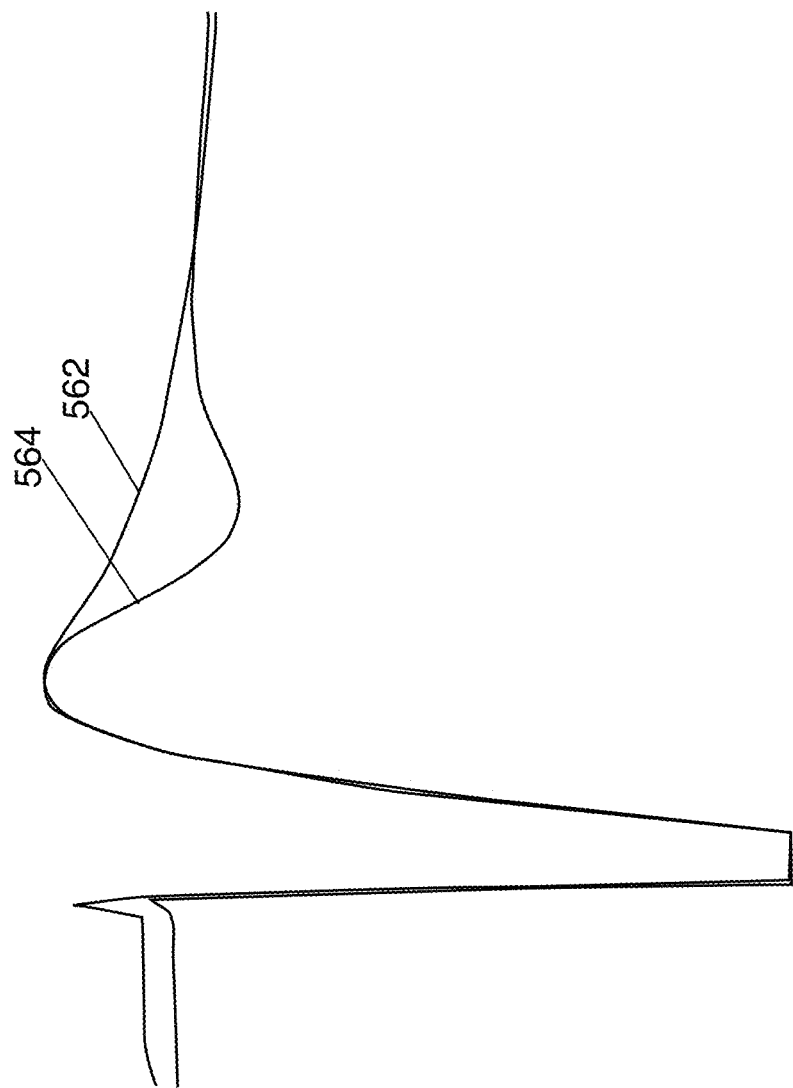

Exemplary couples of a reference curve and an exemplary detection signal curve are presented in FIGS. 10B-10D. FIG. 10B presents a comparison of a detection signal to a reference curve, where the deviation D4 is detected closely (in time) to the beginning of the measurement phase. FIG. 10C presents a comparison of a signal to a reference curve, where a first noticeable deviation D5*b* is detected substantially immediately after the beginning of the measurement phase and a further region of deviation D5*b* is detected afterwards. FIG. 10D presents a comparison of a detection signal to a reference signal, where a substantially large deviation D6 is detected a long time after the beginning of the measurement phase, and may be considered a late reaction of the detector, also known as an after-shock signal.

Reference is now also made to FIGS. 11A-11F, which are graphs of reference time-dependent curves and exemplary respective time-dependent curves of output signals received from a chemical detector of the detector 120 in response to molecules of various explosives carried by the carrier gas and further shaped by the output signal unit 128 before processing to the computing unit 130.

FIGS. 11A-11F depicts reference curves 502, 522, 532, 542, 552, and 562 and respective curves 504, 521, 534, 544, 554 and 564 which are respectively output signals obtained in response to the detection of TNT, Dinitrotoluene (DNT), pentaerythritol tetranitrate (PETN), SEMTEX™, ethylene glycol dinitrate (EGDN), and C4 molecules carried by the carrier gas.

The apparatus described hereinabove may be used as a mobile device for detecting explosives, for example integrated into a wand shaped handheld housing that allows the maneuvering thereof along the body of a suspect and/or an article, for example as described above.

The apparatus described hereinabove may be used as a stationary device for detecting explosives in airports, passenger terminals, harbors, and the like. In such an embodiment, the apparatus may be placed to draw sample air from articles and/or suspects which are passing via an airport, a passenger terminal, a harbor, and the like.

The apparatus described hereinabove may be used for detecting molecules of chemical agents, for example of a chemical weapon. In such an embodiment, the apparatus may be used for alerting and/or alarming a user and/or a monitoring system when such the presence of certain chemical agents is detected.

The apparatus described hereinabove may be activated automatically, for example in response to an instruction received from a controller and/or a sensor, such as a movement sensor, periodically, for example automatically performing a detection cycle every period, and/or manually, for example upon a request of a user.

It should be noted that the aforementioned apparatus may be activated without or substantially without interludes. As the aforementioned apparatus requires only electricity and utility gas for being operational, the aforementioned apparatus may iteratively perform detection cycles, optionally each as depicted in FIG. 3.

The apparatus described hereinabove may be used for detecting molecules which are indicative of food infections, food poisoning, and/or food decay. For example, the presence of nitrates and/or nitrites may be indicative of a bacterial infection.

The apparatus described hereinabove may be used for monitoring manufacturing processes, for example by monitoring a concentration, an absence and/or a presence of one or more compounds. For example, the detection of nitrates from tobacco products may be used for correlation with the amount of tobacco-specific nitrosamines within the tobacco.

The apparatus described hereinabove may be used for detecting narcotics, for example by drawing gas sample from articles and suspects in airports.

According to some embodiments of the present invention, the concentration unit 106, the chromatographic separator 126, and/or the detector 120 are detachable and replaceable. In such an embodiment, the user may select the concentration unit 106, the chromatographic separator 126, and/or the detector 120 which are adapted for detecting a certain analyte.

According to some embodiments of the present invention, the analysis apparatus 100 includes a number of concentration units, for example each as shown at 106, a number of chromatographic separators, for example each as shown at 126, and/or a number of detectors, for example each as shown at 120. In such an embodiment, the analysis apparatus 100 may be configured for drawing a gas sample via a selected set of components, for example via one of the chromatographic separators, one of the detectors, and one of the concentration units. Different sets may be selected for different analytes. In such an embodiment a system of passages and valves is used for directing the gas sample, the utility gas, and/or the utility gas with the analytes, which is also referred to herein as a carrier gas, among the compounds of the selected set.

According to some embodiments of the present invention, a system that comprises a number of detection apparatuses, each as depicted in 100, is provided. Optionally, each one of the detection apparatuses is adapted for detecting one or more different analytes, for example as described above. In such an embodiment, the operator and/or the controller may select which one of the apparatuses to operate according to the analytes she wants to detect and/or to monitor. Optionally, the number of detection apparatuses may share a common component, for example a common gas source, a common inlet, a common outlet, a common pump and the like.

According to some embodiments of the present invention, the analysis apparatus 100 is designed for drawing gas samples from burnt particles. In such an embodiment, the analysis apparatus 100 may be used for analyzing particles which are collected from an article or a suspect, for example using a sniffer device, and burnt, for example in a designated oven. The burnt particles are drawn with a gas sample, for example as described above. In such a manner, the analysis apparatus 100 may be used for analyzing particles having a relatively large diameter.

It is expected that during the life of a patent maturing from this application many relevant systems and methods will be developed and the scope of the term carrier gas, utility/carrier gas source, a pump, a valve, and a chemical detector is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the bonded claims.

Various embodiments and aspects of the present invention as delineated hereinabove and as claimed in the claims section below find experimental support in the following examples.

Reference is now made to the following examples, which together with the above descriptions, illustrate some embodiments of the invention in a non limiting fashion.

In these examples a device as depicted in FIG. 4 and in FIGS. 9A-9E and described above is used. The protocol span was basic but threat related in the aspect of commercial explosives as analytes. The analytes were placed in separate 20 ml glass tubes, 1 gram for each sample. The specimens were heated in an oven to reach 50 deg. Celsius on the outer side of the tube. When tested the sealing cap was removed and a nozzle was inserted for a concentration period of 4 seconds. Each specimen was tested 3 times in order to increase assurance of detection. The tests showed the detection of standard and improvised explosives. The following detection chart indicates which explosives where detected (marked with +) and which explosives where not (marked with −):

| Explosive type detection | Detection |
| --- | --- |
| RDX | + |
| PETN | + |
| TEN Military | + |
| TEN Paraffin | + |
| Gun powder single base | + |
| Gun powder double base | − |
| TNT - flakes | + |
| ANFO | + |
| C-4 | + |
| EGDN - standard solution | + |
| TATP | + |
| UN | + |
| DNT | + |
| NG | + |
| TETRIL | + |

In similar tests, a number of potentially diverting materials were tested:

| Materials | Detection |
| --- | --- |
| Cigarettes smoke | − |
| Diesel fumes | − |
| Acetone | − |
| NaCl | − |

-continued

| Materials | Detection |
|---|---|
| Shoe polish | – |
| Tooth paste | – |
| Alcohol | – |
| White benzene | – |

The ability to avoid false alarms by such diverting materials improves the reliability of the detection as it reduces the number of false positive errors.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for inspecting a gas sample stream, comprising:
    heating a chemical detector to a standby temperature and maintaining said chemical detector in said standby temperature;
    collecting at least one analyte from a gas sample using a concentration element in a chamber while streaming a first amount of carrier gas into a target space of a chemical detector so as to maintain said standby temperature during said collecting; and
    streaming a second amount of carrier gas via said chamber so that said at least one analyte being transferred into said target space after said collecting;
    wherein said carrier gas and said gas sample are respectively streamed and drawn via a common passage which is located between said concentration element and said detection unit;
    wherein said common passage comprises a T shaped tubular element.

2. The method of claim 1, further comprising using at least one detector at said target space for analyzing said at least one analyte.

3. The method of claim 2, wherein said at least one detector comprises an electron capture detector.

4. The method of claim 2, further comprising streaming an amount of said carrier gas via said at least one detector so that reminders of said at least one analyte being removed therefrom.

5. The method of claim 1, wherein said carrier gas and said gas sample are streamed in opposing directions in said chamber.

6. The method of claim 1, further comprising streaming amount of said carrier gas in a chamber comprising said concentration element so that reminders of said at least one analyte being removed therefrom.

7. The method of claim 1, further comprising heating said concentration element to catalyze a release of said at least one analyte from said concentration element.

8. The method of claim 1, wherein said streaming is done toward an outlet, via a chromatographic separator and a detection unit.

9. The method of claim 8, further comprising using said detection unit for detecting at least one of the presence, the absence and the concentration of said at least one analyte.

10. The method of claim 1, wherein said streaming is held during a period of less than 10 seconds.

11. The method of claim 1, wherein said heating starts before said carrier gas is streamed in a detection cycle of less than 1 minute.

12. The method of claim 1, wherein said concentration element is a metallic concentrator.

13. The method of claim 1, wherein said heating brings said concentration element to a temperature of at least 200° C.

14. The method of claim 13, wherein said heating brings said concentration element to said temperature in less than 2 second.

15. The method of claim 1, wherein said common passage is valveless.

16. The method of claim 1, wherein said concentrating element comprises a platinum coil for bonding said at least one analyte.

17. An apparatus for inspecting a gas sample stream, comprising:
    a heating element for heating a chemical detector to a standby temperature and maintaining said chemical detector in said standby temperature;
    a chemical detector;
    a chamber comprising a concentration element;
    a T shaped tubular element located between said concentration element and said chemical detector;
    wherein the concentration element is adapted for collecting at least one analyte from a gas sample streamed via said T shaped tubular element while a first amount of carrier gas is streamed into a target space of said chemical detector so as to maintain said standby temperature during said collecting; and
    a gas source adapted for streaming a second amount of carrier gas via said T shaped tubular element and via said chamber so that said at least one analyte being transferred into said target space after said collecting.

* * * * *